US009468516B2

(12) United States Patent
Sandhu et al.

(10) Patent No.: US 9,468,516 B2
(45) Date of Patent: Oct. 18, 2016

(54) MAGNETIC MEDICAL APPARATUS, KITS, AND METHODS

(75) Inventors: Gurpreet S. Sandhu, Rochester, MN (US); Robert D. Simari, Rochester, MN (US); Nicole P. Sandhu, Rochester, MN (US); Rajiv Gulati, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 911 days.

(21) Appl. No.: 13/013,559

(22) Filed: Jan. 25, 2011

(65) Prior Publication Data

US 2011/0118820 A1    May 19, 2011

Related U.S. Application Data

(63) Continuation of application No. 11/922,172, filed as application No. PCT/US2006/023571 on Jun. 16, 2006, now abandoned, and a continuation-in-part of application No. 11/446,861, filed on Jun. 5, 2006, and (Continued)

(51) Int. Cl.
*A61F 2/30* (2006.01)
*A61F 2/07* (2013.01)
(Continued)

(52) U.S. Cl.
CPC .. *A61F 2/07* (2013.01); *A61F 2/04* (2013.01); *A61F 2/06* (2013.01); *A61F 2/24* (2013.01);
(Continued)

(58) Field of Classification Search
CPC ............... A61F 2002/30079; A61F 2002/077; A61F 2/07
See application file for complete search history.

(56) References Cited

U.S. PATENT DOCUMENTS 3,993,072 A * 11/1976 Zaffaroni ............ A61M 31/002
                                                    128/833
4,335,094 A *  6/1982 Mosbach ............. A61K 9/5094
                                                    424/1.37

(Continued)

FOREIGN PATENT DOCUMENTS

EP        0 884 064 A2   12/1998
EP        0 884 064 A3    6/1999
(Continued)

OTHER PUBLICATIONS

International Search Report issued on Jul. 25, 2008 for PCT/US2006/023571, filed Jun. 16, 2006; 4 pgs.

(Continued)

*Primary Examiner* — Christian Sevilla
*Assistant Examiner* — Seema Mathew
(74) *Attorney, Agent, or Firm* — Mueting, Raasch & Gebhardt, P.A.

(57) ABSTRACT

Medical devices with surfaces on which viable biologic cells are magnetically attracted and retained are disclosed along with methods of magnetic coating. The medical devices can be located in a carrier liquid containing high concentrations of magnetic cells before or after implantation. The carrier liquid with magnetic cells may be contact with the medical device in vitro or in vivo. In either case, the carrier liquid may have a concentration of magnetic cells that is high enough to facilitate coating of the medical device within an acceptable period of time, e.g., several hours or less. Magnetization of medical devices before, during, and/or after implantation and apparatus for performing the same are disclosed. Degaussing of magnetic medical devices is also disclosed.

22 Claims, 6 Drawing Sheets

Related U.S. Application Data a continuation-in-part of application No. PCT/US2004/040242, filed on Dec. 2, 2004.

(60) Provisional application No. 60/691,090, filed on Jun. 16, 2005, provisional application No. 60/526,522, filed on Dec. 3, 2003.

(51) Int. Cl.
| | | |
|---|---|---|
| A61F 2/04 | (2013.01) | |
| A61F 2/06 | (2013.01) | |
| A61F 2/24 | (2006.01) | |
| A61F 2/82 | (2013.01) | |
| A61N 1/05 | (2006.01) | |

(52) U.S. Cl.
CPC .. *A61F 2/30* (2013.01); *A61F 2/82* (2013.01); *A61F 2002/077* (2013.01); *A61F 2002/30079* (2013.01); *A61F 2210/009* (2013.01); *A61N 2001/0585* (2013.01)

(56) References Cited

U.S. PATENT DOCUMENTS

| | | | |
|---|---|---|---|
| 4,503,569 A | 3/1985 | Dotter | |
| 4,685,446 A | 8/1987 | Choy | |
| 4,733,665 A | 3/1988 | Palmaz | |
| 4,804,382 A | 2/1989 | Turina et al. | |
| 5,037,378 A | 8/1991 | Muller et al. | |
| 5,129,883 A | 7/1992 | Black | |
| 5,135,484 A | 8/1992 | Wright | |
| 5,558,642 A | 9/1996 | Schweich, Jr. et al. | |
| 5,655,546 A * | 8/1997 | Halpern | A61F 2/30756 128/898 |
| 5,707,385 A | 1/1998 | Williams | |
| 5,851,218 A | 12/1998 | Lev | |
| 5,882,292 A | 3/1999 | Miyaguchi | |
| 5,906,579 A | 5/1999 | Vander Salm et al. | |
| 5,921,244 A | 7/1999 | Chen et al. | |
| 5,968,070 A | 10/1999 | Bley et al. | |
| 5,980,887 A | 11/1999 | Isner et al. | |
| 6,178,968 B1 | 1/2001 | Louw et al. | |
| 6,203,487 B1 | 3/2001 | Consigny | |
| 6,375,787 B1 | 4/2002 | Lukic | |
| 6,544,276 B1 | 4/2003 | Azizi | |
| 6,575,932 B1 | 6/2003 | O'Brien et al. | |
| 6,585,756 B1 | 7/2003 | Strecker | |
| 6,673,104 B2 | 1/2004 | Barry | |
| 6,905,874 B2 | 6/2005 | Berenson et al. | |
| 6,939,374 B2 | 9/2005 | Banik et al. | |
| 6,939,375 B2 | 9/2005 | Sirhan et al. | |
| 6,978,173 B2 | 12/2005 | Stoll et al. | |
| 7,001,419 B2 | 2/2006 | DiCaprio et al. | |
| 7,223,282 B1 | 5/2007 | Hossainy | |
| 7,846,201 B2 * | 12/2010 | Chorny | A61K 9/5146 424/646 |
| 8,052,744 B2 * | 11/2011 | Girton | A61L 31/146 623/1.39 |
| 8,057,534 B2 * | 11/2011 | Boismier | A61F 2/91 623/1.15 |
| 9,283,095 B2 * | 3/2016 | Tigno, Jr. | A61F 2/82 |
| 2001/0017579 A1 | 8/2001 | Kurata | |
| 2002/0042130 A1 | 4/2002 | Hebbel et al. | |
| 2002/0049495 A1 | 4/2002 | Kutryk et al. | |
| 2002/0082679 A1 | 6/2002 | Sirhan et al. | |
| 2002/0082685 A1 | 6/2002 | Sirhan et al. | |
| 2002/0133225 A1 | 9/2002 | Gordon | |
| 2002/0138100 A1 | 9/2002 | Stoll et al. | |
| 2002/0138154 A1 * | 9/2002 | Li | A61F 2/04 623/66.1 |
| 2002/0198435 A1 | 12/2002 | Paturu | |
| 2003/0082148 A1 | 5/2003 | Ludwig et al. | |
| 2003/0083646 A1 * | 5/2003 | Sirhan et al. | 604/891.1 |
| 2004/0009326 A1 * | 1/2004 | Stefanutti | C09J 7/04 428/137 |
| 2005/0004417 A1 | 1/2005 | Nelson et al. | |
| 2006/0041182 A1 | 2/2006 | Forbes et al. | |
| 2006/0286137 A1 * | 12/2006 | Sandhu | A61F 2/06 424/422 |
| 2007/0027460 A1 * | 2/2007 | Case | A61L 27/02 606/151 |
| 2007/0142907 A1 * | 6/2007 | Moaddeb | A61F 2/2445 623/2.11 |
| 2007/0231393 A1 * | 10/2007 | Ritter | A61K 9/0009 424/489 |
| 2007/0299518 A1 * | 12/2007 | Ruane | A61L 27/34 623/11.11 |
| 2008/0071353 A1 * | 3/2008 | Weber | A61L 31/148 623/1.15 |
| 2009/0118817 A1 * | 5/2009 | Sandhu | A61F 2/06 623/1.39 |
| 2009/0319032 A1 * | 12/2009 | Weber | A61L 31/146 623/1.39 |
| 2010/0198329 A1 * | 8/2010 | Kassab | A61B 17/00491 623/1.13 |
| 2011/0029026 A1 * | 2/2011 | Nicolella | A61F 2/28 606/86 R |
| 2011/0230952 A1 * | 9/2011 | Kassab | A61B 17/12113 623/1.11 |
| 2014/0324158 A1 * | 10/2014 | Martin | A61L 31/005 623/1.38 |

FOREIGN PATENT DOCUMENTS

| | | |
|---|---|---|
| EP | 0 884 064 B1 | 4/2002 |
| GB | 2 352 635 A | 2/2001 |
| JP | 5-184681 | 7/1993 |
| JP | 2001-517973 | 10/2001 |
| JP | 2003-082465 | 3/2003 |
| JP | 2007-000975 A | 1/2007 |
| WO | WO 94/23786 A1 | 10/1994 |
| WO | WO 98/09678 A1 | 3/1998 |
| WO | WO 01/93939 A1 | 12/2001 |
| WO | WO 02/056799 A2 | 7/2002 |
| WO | WO 02/080815 A2 | 10/2002 |
| WO | WO 02/056799 A3 | 12/2002 |
| WO | WO 02/080815 A3 | 1/2003 |
| WO | WO 03/037400 A2 | 5/2003 |
| WO | WO 2004/093643 A2 | 11/2004 |
| WO | WO 03/037400 A3 | 2/2005 |
| WO | WO 2004/093643 A3 | 4/2005 |
| WO | WO 2005/056073 A2 | 6/2005 |
| WO | WO 2005/056073 A3 | 9/2005 |
| WO | WO 2006/005015 A2 | 1/2006 |
| WO | WO 2006/005015 A3 | 4/2006 |

OTHER PUBLICATIONS

International Search Report issued on Jul. 14, 2005 for PCT/US2004/040242, filed Feb. 12, 2004; 5 pgs.

International Preliminary Report on Patentability issued Mar. 30, 2006 by the PCT, for Patent Application No. PCT/US2004/040242, filed Feb. 12, 2004.

International Preliminary Report on Patentability issued Mar. 31, 2009 by the PCT, for Patent Application No. PCT/US2006/023571, filed Jun. 16, 2006.

Lu et al., "The effect of magnetic stent on coronary restenosis after percutaneous transluminal coronary angioplasty in dogs," *Chin. Med. J. (Engl.)*, Aug. 2001; 114(8): 821-3.

\* cited by examiner

MAGNETIC MEDICAL APPARATUS, KITS, AND METHODS

RELATED APPLICATIONS

The present application is a continuation application of U.S. Ser. No. 11/922,172, filed Sep. 16, 2008 and titled MAGNETIC MEDICAL APPARATUS, KITS, AND METHODS which is a U.S. National Stage Application of International Application No. PCT/US2006/023571, filed Jun. 16, 2006 and titled MAGNETIC MEDICAL APPARATUS, KITS, AND METHODS, which claims the benefit under 35 U.S.C. §119(e) of U.S. Provisional Patent Application No. 60/691,090, filed Jun. 16, 2005, and titled MEDICAL DEVICES WITH DISTRIBUTED MAGNETIC FIELDS AND METHODS OF MANUFACTURING SAME, all of which are hereby incorporated by reference in their entirety.

International Application No. PCT/US2006/023571 is also a continuation-in-part of U.S. patent application Ser. No. 11/446,861, filed on 5 Jun. 2006, titled KITS, APPARATUS AND METHODS FOR MAGNETICALLY COATING MEDICAL DEVICES WITH LIVING CELLS, which claims the benefit of U.S. Provisional Application No. 60/691,090, filed on 16 Jun. 2005, titled MEDICAL DEVICES WITH DISTRIBUTED MAGNETIC FIELDS AND METHODS OF MANUFACTURING THE SAME and which is a continuation-in-part of PCT/US2004/040242, filed on 2 Dec. 2004, titled KITS, APPARATUS AND METHODS FOR MAGNETICALLY COATING MEDICAL DEVICES WITH LIVING CELLS, which claims the benefit of U.S. Provisional Application No. 60/526,522, filed on 3 Dec. 2003, titled COATING MAGNETIC MEDICAL DEVICES WITH LIVING CELLS, all of which are hereby incorporated by reference in their entireties.

A recurring issue in the field of medical devices, especially implantable medical devices, is the need to provide surfaces that are compatible with the environment in which they are contained.

Problems associated with implanted medical devices that include surfaces in contact with a patient's bloodstream may include, for example, the risk of acute thrombosis and chronic instability—such as calcification—of the implant surface. Surfaces of e.g., prostheses that are implanted as part of the circulatory system can be a crucial factor governing the functionality and patency rates of the synthetic prostheses. Poor blood compatibility of these surfaces is almost always a predominant reason for the limitations of these implants, such as the loss of heart valve functionality over time or poor patency rates in small diameter conduits due to acute thrombosis or intimal hyperplasia. Attempts to modify the surfaces of synthetic grafts to overcome the patency problems associated with thrombosis or intimal hyperplasia have generally shown poor long-term outcomes, as these surfaces are unable to maintain a sustained anti-thrombogenic bioactivity as discussed in, e.g., U.S. Patent Application Publication No. US 2003/0082148 A1 (Ludwig et al.).

One surface modification approach which has been utilized for blood contacting implants such as synthetic grafts is "endothelial seeding". In vitro endothelial seeding utilizes viable endothelial cells which are seeded onto the blood contacting surface of a prosthesis such as the lumen surface of a vascular graft to mimic the surface of natural blood vessels. This surface modification technique aims to produce a confluent, biologically active surface of viable endothelial cells which, by definition, is anti-thrombogenic.

Problems arise, however, in the retention of suitable cells on the surfaces of the devices. Techniques aimed to improve the retention of endothelial cells on vascular grafts are described in, e.g., U.S. Pat. No. 5,037,378 (Muller et al.). In another approach (described in, e.g. U.S. Pat. No. 4,804,382 (Turina et al.)), endothelial cells are applied to a semipermeable membrane in which the pores are filled with aqueous gels to allow endothelial cell coverage. Another approach to prevent endothelial loss after seeding is to modify the graft lumen surface to make it sufficiently adhesive for endothelial cells. Surface modification methods include the interstitial deposition of protein glues or matrices, the adsorption of proteins to the graft surface, and the covalent immobilization of adhesion-promoting ligands, peptides, or proteins onto functional groups introduced by chemical modification or gas plasma treatment. Another method for preventing the loss of endothelial cells and for improving patency rates of synthetic grafts involves using shear stress to pre-condition the endothelial layer of a synthetic graft.

Still another set of methods for retaining endothelial and other cells on graft surfaces are described in U.S. Patent Application Publication No. US 2003/0082148 A1 (Ludwig et al.). One set of techniques disclosed in that reference involves, e.g., the use of ligands for in vivo recruitment of target cells, where the ligands include molecules that are binding partners to a molecule presented on the surfaces of the target cells. Another set of techniques involves in vivo recruitment of target cells using magnetic forces, where the target cells are magnetically charged and released within the bloodstream of the patient. As the magnetically charged target cells pass near magnetic graft, they are captured on the surface.

Unfortunately, however, in vivo recruitment techniques suffer from a number of disadvantages. One significant disadvantage is the inability to determine whether the magnetic forces exhibited by the surfaces are sufficient to attract target cells before implantation. A failure to properly magnetize a device including magnetic material that is not permanently magnetic may result in less than optimal in vivo recruitment.

Another potential disadvantage is the time required to recruit significant numbers of target cells to the desired surfaces. Days or weeks may be required to adequately cover the exposed surfaces of the device. Furthermore, even after significant periods of time, the target cells may be attached at low density over the surfaces, resulting in less than optimal performance. If the surfaces are located in areas of limited or no blood flow, then recruitment may be further hampered or prevented.

One issued faced when attempting to use magnetic fields to coat medical devices with magnetic cells as defined in the above-identified documents is the ability to provide magnetic material in or on a vascular graft. Many vascular grafts are constructed of woven fabrics in contrast to the metals or stiffer polymeric structures used to construct stents or other medical devices. Because the fabrics used in vascular grafts may not be constructed of magnetic materials and may not be amenable to receiving and retaining metallic coatings that could provide the desired magnetic coatings, imparting magnetic fields capable of attracting and retaining magnetic cells may be difficult.

Another potential issue faced when attempting to use magnetic attraction may be found in the logistics of imparting magnetic attraction to an existing medical device or to body locations where no medical device is to be implanted.

SUMMARY OF THE INVENTION

The present invention provides medical devices with surfaces on which viable biologic cells and other magnetic materials are magnetically attracted and retained. Methods of the present invention involve attraction and retention of magnetic cells and other magnetic materials on magnetic contact surfaces of medical devices.

The potential advantages of magnetically coating the fabric of a vascular graft may include the ability to provide grafts with significantly smaller inner diameters. Conventional vascular grafts are typically limited to inner diameters of 6 millimeters (mm) or more because of occlusion problems. Using magnetic attraction to coat the grafts in vivo may allow for grafts with smaller lumen diameters, e.g., 4 mm or less.

In some embodiments of the medical devices of the present invention, a tubular fabric structure (e.g., a vascular graft) may include one or more magnetic strands woven or knitted into the structure of the vascular graft. The magnetic strands may be constructed of magnetic material (e.g., the strand could be a thin wire constructed of nickel or another magnetic material) or they may be constructed of a non-magnetic core with a magnetic coating located thereon (e.g., a polymeric core with a coating of magnetic material). It may be preferred that magnetic material in the strands be coated in a biocompatible material as described in the above-identified documents.

In other embodiments, tubular fabric structures may be coated with a non-magnetic binder containing magnetic particles distributed therein. Such a magnetic coating may be provided on an exterior surface of the structure, an interior surface of the structure (lining the lumen), or both the exterior and interior surfaces.

In other embodiments, the present invention may include stents or other structures that include spaced-apart struts. A magnetic coating in the form of a non-magnetic binder in which magnetic particles are distributed may be provided to bridge the openings between the struts. It may be preferred that such a skin layer be flexible—it may also be preferred that such a skin layer be elastomeric. The struts may preferably be encased within the non-magnetic binder.

In still other embodiments, the present invention may provide magnetic medical devices that include a fractured metallic coating to provide dispersed magnetic fields on a magnetic contact surface. The dispersed magnetic fields are associated with discrete islands of the metallic coating that are separated from each other by fractures in the metallic coating.

In still other embodiments, the present invention may include magnetic sleeves or sheets that may be used alone or in connection with other medical devices to impart magnetic attraction capabilities to an existing medical device or to provide magnetic attraction at locations where no other medical device is located. The sleeves or sheets may preferably be formed of a non-magnetic binder in which magnetic particles are distributed. The sleeves or sheets may preferably be flexible, elastomeric, porous, nonporous, biodegradable, etc. The sleeves or sheets may be held in place using another medical device (e.g., stent, graft, etc.) or they may be secured by any other suitable technique or techniques (e.g., adhesives, sutures, receptor-ligands, etc.).

One potential advantage of the present invention is the ability to rapidly attract and attach large numbers of magnetic cells and other magnetic materials to the magnetic contact surfaces of a medical device. This is possible because the device can be located in a carrier liquid containing high concentrations of magnetic cells/material before or after implantation. The carrier liquid with magnetic cells/material may be in contact with the medical device in vitro or in vivo. In either case, it may be preferred that the carrier liquid have a concentration of magnetic cells/material that is high enough to facilitate coating of the medical device within an acceptable period of time, e.g., several hours or less.

Although described herein in the context of attracting magnetic cells, it should be understood that the medical devices, methods, and kits of the present invention may be used to attract magnetic materials other than cells, e.g., drugs, therapeutic substances, sub-cellular particles, etc.

If the magnetic coating is performed in vivo, it may be preferred that the carrier liquid with magnetic cells be delivered to a defined volume in which the medical device is located. If the medical device is implanted within, e.g., a blood vessel, the defined volume may be created by using a catheter to seal the vessel on one or both sides of the implanted medical device, followed by delivery of the carrier liquid to the location of the implanted medical device.

Another potential advantage of the present invention is that the medical devices may be located in any suitable location within the body and coated with magnetic cells after implantation, i.e., the medical devices and methods may be used in blood vessels, but the potential locations are not limited to blood vessels. For example, the medical devices may be located and magnetically coated within the gastrointestinal tract, salivary glands, bile ducts, pancreatic ducts, renal system (kidney, ureters, bladder, urethra, etc.), airways in lungs, conduits in the brain and spinal cord, surgically created conduits or lumens in an organ, congenital abnormalities in any organ, etc.

Another potential advantage of the present invention is that medical devices constructed of metals and/or metal alloys may be easily and quickly magnetized by exposure to a magnetic field (if the metals or metal alloys do not inherently exhibit magnetic fields). In some embodiments, the apparatus and methods of the present invention provide the ability to magnetize a medical device as part of the implantation process or to magnetize the medical device in vivo. In some instances, it may be possible to use known medical devices such as, e.g., stents, heart valves, etc. in connection with the present invention.

Yet another potential advantage of the present invention is the ability to demagnetize an implanted medical device after magnetically coating the medical device by, e.g., locating a degaussing element proximate the medical device in vivo after a selected period of time, e.g., 24 hours to 48 hours. By magnetically coating the medical device, the advantages associated with magnetic coating as discussed herein may be obtained and any potential disadvantages associated with leaving a magnetized medical device may be alleviated by demagnetizing the medical device after the magnetically attracted biologic cells have formed alternative attachments to the medical device.

Still another potential advantage of some embodiments of the present invention is that cells can be magnetically attracted to and retained on the medical devices without requiring additional modifications for cellular attachments such as receptor-ligand binding, antigen-antibody interactions, or other coatings (such as, e.g., fibronectin) to obtain adequate cell adhesion. Examples of some such binding techniques that may be avoided by use of the present invention include, but are not limited to, e.g., ligand binding, fibronectin, antibodies, proteins, etc.

Another potential advantage of the present invention is that, in some embodiments, all of the magnetic contact surfaces of the medical devices can be coated by the magnetic cells. The ability to magnetically attach cells to all magnetic surfaces may provide improved coverage over all surfaces, even those located in areas not otherwise easily accessible.

Still another potential advantage may, in some embodiments, be found in the ability to effectively monitor attraction and retention of the magnetic cells on the magnetic contact surfaces of the medical devices. Such monitoring may preferably be performed before using the medical device (e.g., implanting it in a patient). If the cells are unevenly or insufficiently retained on the medical device, steps can be taken to improve attraction and/or retention before the device is implanted or to simply discard the device.

One issue that may be faced when attempting to use magnetic fields to coat medical devices with magnetic cells is the ability to coat significant portions of the devices with improved uniformity. In some magnetic medical devices, the device itself may function as a unitary magnet with one (or only a few) magnetic poles. Because the magnetic field strength is concentrated at each pole, the magnetic cells may be preferentially attracted to the poles, leaving substantial portions of the device uncoated with the magnetic cells.

One approach to addressing this potential issue is the provision of dispersed magnetic fields over the surfaces of the device to be coated. These dispersed magnetic fields can be achieved in a variety of manners. For example, the device itself can be constructed of non-magnetic binder material in which particles of magnetic materials are dispersed such that they are embedded in the structure of the device. In still another embodiment, the device can be supplied with a coating of non-magnetic binder material in which particles of magnetic material are dispersed. In other embodiments, the magnetic material used for the magnetic fields may be provided in a discontinuous coating of magnetic material where the discontinuous areas of coated magnetic material form discrete separated islands on the device, with each discrete island functioning as a separate magnet.

The common effect of the embodiments exhibiting dispersed magnetic fields is that the magnetic particles or discrete islands of magnetic materials each preferably function as an individual magnet with north and south poles. Because these smaller magnets each possess their own magnetic fields, the magnetic field strength is dispersed based on the location and/or distribution of the magnets (i.e., magnetic particles and/or discrete islands of magnetic material) over the device as opposed to being concentrated at only a few poles. The result is that magnetic cells may be attracted over the surface of the device according to the location and/or distribution of the magnets.

The distributed magnetic fields exhibited in some embodiments of devices of the present invention may preferably result in reduced magnetic field strength at any one location on the device as compared to other devices. For example, it may be possible to achieve desired levels of magnetic attraction of magnetic cells with magnetic field strengths that are in the range of 10 Gauss or less, preferably 5 Gauss or less, or even 1 Gauss or less. It should, however, be understood that stronger distributed magnetic fields may also be used in connection with the present invention.

Another potential issue that may be faced when attempting to use magnetic fields to coat medical devices with magnetic cells is the ability to provide magnetic material in or on a vascular graft. Many vascular grafts are constructed of woven fabrics in contrast to the metals or stiffer polymeric structures used to construct stents or other medical devices. Because the fabrics used in vascular grafts may not be constructed of magnetic materials and may not be amenable to receiving and/or retaining metallic coatings that could provide the desired magnetic coatings, imparting magnetic fields capable of attracting and retaining magnetic cells may be difficult.

The potential advantages of magnetically coating the fabric of a vascular graft may include the ability to provide grafts with significantly smaller inner diameters. Conventional vascular grafts are typically limited to inner diameters of 6 millimeters (mm) or more. Vascular grafts with smaller lumens typically clot or occlude quickly due to their limited size.

In one aspect, the present invention provides an implantable medical apparatus that includes an implantable medical device; and a flexible magnetic sleeve located over an outer surface of the medical device, wherein the flexible sleeve is constructed of non-magnetic binder containing magnetic particles dispersed within the non-magnetic binder.

In another aspect, the present invention provides an implantable medical apparatus that includes an implantable medical device having a tubular structure; and a flexible magnetic sleeve located within the tubular structure of the medical device, wherein the flexible sleeve is constructed of non-magnetic binder containing magnetic particles dispersed within the non-magnetic binder.

In another aspect, the present invention provides an implantable magnetic sleeve that includes a flexible tubular body formed of a non-magnetic binder containing magnetic particles dispersed within the non-magnetic binder, wherein the non-magnetic binder is biodegradable, and wherein the flexible tubular body comprises a porous wall.

In another aspect, the present invention provides an implantable magnetic device that includes a cylindrical body defining a lumen formed therethrough, wherein the body has a tubular structure; a coating including a non-magnetic binder applied to a wall of the tubular structure; and a plurality of magnetic particles dispersed in the coating.

In another aspect, the present invention provides a vascular graft including a tubular body defining a lumen formed therethrough, wherein the body has a fabric structure; one or more magnetic strands woven into the fabric structure, wherein the one or more magnetic strands include magnetic material.

In another aspect, the present invention provides a vascular graft that includes a tubular body defining a lumen formed therethrough, wherein the body has a fabric structure; a coating including a non-magnetic elastomeric binder applied to the fabric structure; and a plurality of magnetic particles dispersed in the non-magnetic elastomeric binder, wherein the plurality of magnetic particles is arranged in a selected distribution within the coating.

In another aspect, the present invention provides an implantable medical device with a magnetic contact surface in the form of a plurality of discrete islands of magnetic material located on a substrate, wherein the magnetic material is in the form of a metallic coating on the substrate and wherein the discrete islands are separated by fractures in the metallic coating.

In another aspect, the present invention provides a kit for magnetically coating a medical device in vivo, the kit including an implantable medical device or apparatus (in the form of, e.g., a sleeve, graft, etc.); and means for enclosing a defined volume in vivo in which the implantable medical device or apparatus is located when implanted.

In another aspect, the present invention provides a kit for magnetically coating a medical device in vivo, the kit including an implantable medical device or apparatus (in the form of, e.g., a sleeve, graft, etc.); and a catheter for creating a defined volume in a biologic conduit in vivo, wherein the catheter includes at least one seal capable of closing the biologic conduit when deployed within the conduit; a carrier liquid lumen extending from a proximal end of the catheter to a location proximate the at least one seal; and an opening in the carrier liquid lumen proximate the at least one seal, wherein carrier liquid in the carrier liquid lumen is capable of exiting the catheter proximate the seal.

In another aspect, the present invention provides a kit for magnetically coating a medical device in vivo, the kit including an implantable medical device having a magnetic contact surface; and means for enclosing a defined volume in vivo in which the implantable medical device is located when implanted.

In another aspect, the present invention provides a kit for magnetically coating a medical device in vivo. The kit includes an implantable medical device with a magnetic contact surface and a catheter for creating a defined volume in a biologic conduit in vivo. The catheter may include at least one seal capable of closing the biologic conduit when deployed within the conduit; a carrier liquid lumen extending from a proximal end of the catheter to a location proximate the at least one seal; and an opening in the carrier liquid lumen proximate the at least one seal, wherein carrier liquid in the carrier liquid lumen is capable of exiting the catheter proximate the seal.

In another aspect, the present invention provides an apparatus for magnetizing a medical device in vivo, the apparatus including a medical grade catheter with a proximal end and a distal end; and a magnetic field generator operably attached to the catheter, wherein the magnetic field generator is located proximate the distal end of the catheter, and wherein the magnetic field generator can be advanced through a biologic conduit of a subject.

In another aspect, the present invention provides a kit for magnetizing a medical device in vivo, the kit including an implantable medical device with magnetic material; and a magnetizing apparatus for magnetizing the magnetic material of the implantable medical device in vivo, the magnetizing apparatus including a medical grade catheter with a proximal end and a distal end and a magnetic field generator operably attached to the catheter, wherein the magnetic field generator is located proximate the distal end of the catheter, and wherein the magnetic field generator can be advanced through a biologic conduit of a subject.

In another aspect, the present invention provides an apparatus for magnetizing an implantable medical device, the apparatus including an elongated body having a proximal end and a distal end, wherein the elongated body includes a lumen extending from the proximal end to the distal end; and a magnetic field generator located proximate the proximal end of the elongated body, wherein a medical device advanced through the lumen from the proximal end towards the distal end passes through a magnetic field generated by the magnetic field generator.

In another aspect, the present invention provides a kit for magnetizing a medical device, the kit including an implantable medical device with magnetic material; and a magnetizing apparatus for magnetizing an implantable medical device, the magnetizing apparatus including an elongated body with a proximal end and a distal end, wherein the elongated body includes a lumen extending from the proximal end to the distal end; and a magnetic field generator located proximate the proximal end of the elongated body, wherein a medical device advanced through the lumen from the proximal end towards the distal end passes through a magnetic field generated by the magnetic field generator.

In another aspect, the present invention provides a method of magnetically coating an implanted medical device in vivo by providing a carrier liquid with a plurality of magnetic cells, wherein each cell of the plurality of magnetic cells is a viable biologic cell. The method further includes contacting the implanted medical device with the carrier liquid in vivo, wherein the magnetic cells are present in the carrier liquid at a concentration of 1000 cells per milliliter or higher.

In another aspect, the present invention provides a method of magnetically attaching cells to an implantable medical device by locating an implantable medical device in a carrier liquid containing a plurality of magnetic cells in vitro, wherein each cell of the plurality of magnetic cells is a viable biologic cell, and wherein a plurality of the plurality of magnetic cells are magnetically attracted to and retained on the implantable medical device. The method further includes implanting the implantable medical device in a body after the plurality of magnetic cells are magnetically attracted to and retained on the implantable medical device.

In another aspect, the present invention provides a medical device having a plurality of magnetic cells magnetically attracted to and retained on a magnetic contact surface of the medical device, wherein the medical device is manufactured by associating a magnetic charge with a plurality of cells, wherein the plurality of cells become the plurality of magnetic cells, and wherein each cell of the plurality of magnetic cells is a viable biologic cell and locating the magnetic contact surface of the medical device in a carrier liquid containing the plurality of magnetic cells in vitro, wherein the plurality of magnetic cells are magnetically attracted to and retained on the magnetic contact surface of the medical device.

In another aspect, the present invention provides a method of magnetizing a medical device, the method including locating a magnetic field generator proximate an implanted medical device in vivo, and generating a magnetic field using the magnetic field generator, wherein the medical device includes a magnetic contact surface.

In another aspect, the present invention provides a method of demagnetizing a medical device, the method including locating a degaussing element proximate an implanted medical device in vivo, wherein the medical device includes a magnetic contact surface exhibiting a magnetic field, and degaussing the implanted medical device using the degaussing element, wherein the magnetic field strength exhibited by the magnetic contact surface is reduced after the degaussing.

In another aspect, the present invention provides a method of magnetizing an implantable medical device during implantation into a subject, the method including providing a magnetic field proximate a proximal end of an elongated body; passing an implantable medical device through a lumen in the elongated body, wherein the implantable medical device includes magnetic material that passes through the magnetic field such that the medical device includes a magnetic contact surface; and implanting the medical device at an in vivo location after passing the medical device through a distal end of the elongated body.

In another aspect, the present invention provides a vascular graft that includes a cylindrical body defining a lumen formed therethrough, wherein the body includes a tubular fabric structure; and one or more magnetic strands woven into the fabric structure, wherein the one or more magnetic strands include magnetic material.

In another aspect, the present invention provides a vascular graft having a cylindrical body defining a lumen formed therethrough, wherein the body includes a tubular fabric structure; a coating including a non-magnetic elastomeric binder applied to the fabric structure; and a plurality of magnetic particles dispersed in the non-magnetic elastomeric binder, wherein the plurality of magnetic particles is arranged in a selected distribution within the coating.

These and other features and advantages of the present invention may be described in more detail below with respect to some illustrative embodiments of the invention.

DETAILED DESCRIPTION OF ILLUSTRATIVE EMBODIMENTS OF THE INVENTION

In the following detailed description of illustrative embodiments, reference is made to the accompanying drawings that form a part hereof, and in which are shown, by way of illustration, specific embodiments in which the invention may be practiced. It is to be understood that other embodiments may be utilized and structural changes may be made without departing from the scope of the present invention. Furthermore, like reference numbers denote like features in the different figures.

It should be noted that as used herein and in the appended claims, the singular forms "a", "and", and "the" include plural referents unless the context clearly dictates otherwise. Thus, for example, reference to "a magnetic cell" includes a plurality of such cells and reference to "the magnetic contact surface" includes reference to one or more magnetic contact surfaces and equivalents thereof known to those skilled in the art.

Medical Devices with Magnetic Contact Surfaces

Figure 1:
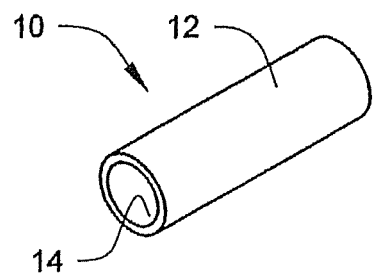
FIG. 1 is a perspective view of one exemplary medical device according to the present invention.

FIG. 1 depicts one illustrative embodiment of a medical device 10 that can be used in connection with the present invention. The depicted device 10 includes an exterior surface 12 and an interior surface 14 that defines, at least in part, a lumen or passageway formed through the device 10. The device 10 may be broadly described as a stent and, although depicted as a solid tubular object, it will be understood that the device 10 may be constructed as a slotted metal tube, wire mesh structure, etc. If provided in the form of a stent as shown, the device 10 may be used to prop open a blood vessel or other tubular structure such as, e.g., bile duct, ureter, etc. The stent may further be designed to open under force using, e.g., an inflatable balloon, or, alternatively, to be self-expanding as is known in the art. Examples of only a few stent designs can be seen in, e.g., U.S. Pat. No. 4,733,665 (Palmaz), U.S. Pat. No. 4,503,569 (Dotter), etc.

Although described herein in connection with a medical device 10 in the form of a stent as depicted in FIG. 1, it should be understood that the medical devices of the present invention may include any medical device that comes in contact with biological material of a living body. In one broad class of medical devices, the present invention may find use with implantable medical devices, i.e., medical devices designed for implantation in an animal or human body. Examples of some suitable implantable medical devices include, but are not limited to, stents, synthetic vascular grafts, prostheses for other biologic conduits (e.g., neurologic, gastrointestinal, renal, endocrine, pulmonary, urologic, etc.), heart valves, artificial hearts, left ventricular assist devices, coronary device leads (for, e.g., pacemakers, defibrillators, etc.), arterio-venous fistulas for dialysis, etc.

In other applications, coils used to embolize and occlude aneurysmal sacs in blood vessels or to occlude blood vessels supplying malignant tumors may be magnetically coated with cells to expedite healing in aneurysms or the occlusion of vessels to tumors. Devices for treating endovascular leaks (holes/ruptures in blood vessels, valves or heart chambers) may also be magnetically coated with cells to facilitate healing and reduce thrombosis. Magnetic devices may also be used to localize cells for treating malignancies in, e.g., organs. Magnetic devices and cells (that, e.g., produce therapeutic agents) may also be placed in blood vessels that supply a tumor.

Furthermore, the medical devices of the present invention may be used in ex vivo applications where surfaces of the devices come into contact with biologic materials (e.g., blood) outside of the body of the subject providing the biologic fluids. Examples of such medical devices may include, e.g., artificial organs, blood pumps, etc.

Both the exterior surfaces 12 and the internal surfaces 14 of the medical device 10 may be considered "contact surfaces" in connection with the present invention. The term "contact surfaces," for the purposes of the present invention, means any surface that can contact a carrier liquid in which the medical device is located for coating. For example, if the device 10 is a stent, any intermediate surfaces of wires, mesh structures, etc. that may be used to construct the device 10 and that extend between what might be defined as the exterior surface 12 and the interior surface 14 may also be considered "contact surfaces" for the purposes of the present invention, provided those surfaces are exposed to and can contact a carrier liquid in which the medical device 10 is placed during the coating process.

In connection with the present invention, it may be preferred that all of the contact surfaces of the medical devices of the present invention may exhibit magnetic fields such that they can magnetically attract and retain objects such as cells using magnetic forces. Contact surfaces of medical devices according to the present invention that exhibit magnetic fields are described as "magnetic contact surfaces." In some instances, it may be preferable to provide a medical device in which only some or portions of some of the contact surfaces on the medical device exhibit magnetic fields (i.e., are magnetic contact surfaces).

The medical devices of the present invention may be made of any suitable material (including, e.g., polymeric materials, metals, metal alloys, ceramics, composites, etc.) provided that the contact surfaces of the medical devices that are to be magnetically coated exhibit magnetic fields capable of attracting and retaining magnetic cells as described herein. To exhibit magnetic fields, the medical devices of the present invention preferably include one or more materials that are magnetic, i.e., that either exhibit a permanent magnetic field or that are capable of exhibiting a temporary magnetic field.

The entire medical device 10, or selected portions thereof, may be manufactured from the one or more magnetic materials. For example, a predetermined quantity of magnetite or an alloy thereof may be included in the construction of the device 10. Other materials may be utilized in addition to or in place of magnetite to provide the desired magnetic properties. Such materials may be temporary magnetic materials or permanent magnetic materials. Some examples of suitable magnetic materials include, e.g., magnetic ferrite or "ferrite" which is a substance consisting of mixed oxides of iron and one or more other metals, e.g., nanocrystalline cobalt ferrite. However, other ferrite materials may be used.

Other magnetic materials which may be utilized in the construction of the device 10 may include, but are not limited to, ceramic and flexible magnetic materials made from strontium ferrous oxide which may be combined with a polymeric substance (such as, e.g., plastic, rubber, etc.); NdFeB (this magnetic material may also include Dysprosium); neodymium boride; SmCo (samarium cobalt); and combinations of aluminum, nickel, cobalt, copper, iron, titanium, etc.; as well as other materials.

Where the device 10 is made of metals such as, e.g., stainless steel, nickel titanium alloys (e.g., NITINOL), etc. or other magnetizable materials, the magnetic contact surfaces of the device may be rendered sufficiently magnetic by subjecting the magnetizable material to a sufficient electric and/or magnetic field. Such a field may imbue the magnetic contact surfaces (or a portion thereof) with magnetic properties without the need to include the permanent magnetic materials described above.

In some embodiments, the magnetic coating surfaces of the medical devices to be coated with magnetic cells through magnetic attraction and retention may consist essentially of one or more metals and/or metal alloys, e.g., stainless steel, nickel titanium alloy, etc. In another manner of characterizing the present invention, the magnetic contact surfaces of the medical device may consist essentially of one or more magnetic materials, where the magnetic materials are permanently magnetic or not as described herein. In still another manner of characterizing the invention, the magnetic contact surfaces of the device may include one or more magnetic materials dispersed in a non-metallic binder.

It may be preferred that medical devices of the present invention include a magnetizable coating such as, e.g., nickel or other materials with a similar susceptibility to magnetization, regardless of whether the body of the medical device includes magnetic or magnetizable materials. For example, it may be preferred that the body of the medical device (e.g., a stent) be constructed of stainless steel that is plated with nickel to increase the magnetic field exhibited by the medical device after magnetization.

If the medical device 10 is designed to be implanted within a human or animal body, its contact surfaces are preferably biocompatible. Unfortunately, many magnetic materials may not be biocompatible. The non-biocompatible magnetic materials may preferably be coated with a biocompatible material that does not significantly limit or interfere with the magnetic fields emanating from the magnetic materials in the medical device such that the magnetic contact surfaces exhibit the desired magnetic fields in the presence of the coating. Biocompatible coatings for use as magnetic contact surfaces on medical devices of the present invention include various biocompatible polymers, metals, and other synthetic, natural, or biologic materials.

In some instances, it may be desirable to provide magnetic contact surfaces that, in addition to exhibiting a magnetic field capable of attracting and retaining a magnetic cell, may also include materials that provide for molecular binding in addition to magnetic attraction and retention. Such molecular binding may be targeted to the same cells as the magnetic cells or to different cells, i.e., cells other than those that are magnetized. For example, the magnetic contact surfaces may also be functionalized to allow for the attachment of cell binding ligands, as well as other molecules such as, e.g., cell mobilization enhancer molecules, molecules for cellular retention and spreading, molecules for cell differentiation, pharmaceutical compounds, etc. In some medical devices of the present invention, it may be desirable to functionalize surfaces of the medical device that are not magnetic contact surfaces whether or not the magnetic contact surfaces are themselves functionalized.

The functionalization of a surface may involve, e.g., gas plasma treatment, chemical modification, photochemical modification, chemical modification through y-radiation activation, co-polymerization with molecules containing functional groups, as well as other surface modification techniques known in the art. The surface to be modified may, for example, be subject to ozonolysis to introduce carbonyl or other reactive groups thereon that will facilitate the attachment of ligands of interest to the chosen surface. In other instances, the surface may be subjected to treatment with acid or base solutions to form hydroxyl and/or carboxylic acid functionalities thereon. Functionalization of the surface to be modified may also be achieved by coating the surface with a layer of polymeric material having a desired functionality. Such polymer layers may include, for example, polyamines such as poly(L-lysine) and poly(L-glutamine) to provide amine functionalities on the specified surface.

Figure 2:
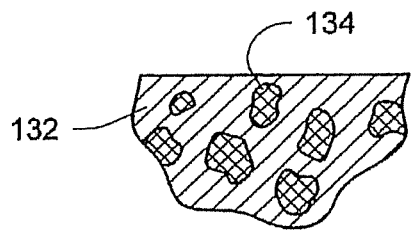
FIG. 2 is an enlarged cross-sectional view of another exemplary embodiment of a magnetic device including magnetic particles dispersed within a non-magnetic medium.

As discussed herein, it may be beneficial to provide dispersed magnetic fields over the magnetic contact surfaces of the device to be coated. These dispersed magnetic fields can be achieved in a variety of manners. For example, the body of the medical device itself can be constructed of non-magnetic binder material in which particles of magnetic materials are dispersed such that they are embedded in the structure of the device. FIG. 2 is an enlarged cross-sectional view of a device that includes magnetic particles 134 dispersed within a non-magnetic medium 132. The non-magnetic medium 132 may preferably be, e.g., polymeric, metallic (but non-magnetic), etc. As a result, the magnetic fields emanating from the magnetic contact surfaces in such medical devices come from the magnetic particles 134 dispersed within the body of the device itself.

Figure 3:
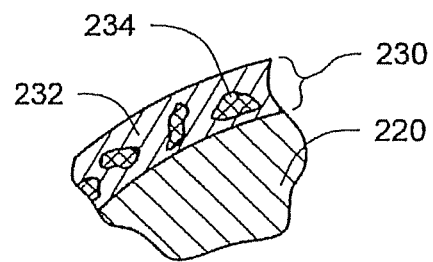
FIG. 3 is an enlarged cross-sectional view of another exemplary magnetic device that includes a coating including a non-magnetic binder in which magnetic particles are dispersed.

In other embodiments, the magnetic contact surfaces of the medical devices of the present invention may be supplied with a coating of non-magnetic binder material in which particles of magnetic material are dispersed to obtain magnetic contact surfaces with dispersed magnetic fields. FIG. 3 is an enlarged cross-sectional view of a device 220 with a coating 230 formed by a non-magnetic binder 232 in which magnetic particles 234 are dispersed. The non-magnetic binder 232 may be, e.g., polymeric, metallic (but non-magnetic), etc.

In another embodiment, the magnetic material used for the dispersed magnetic fields may be provided in a discontinuous coating of magnetic material where the discontinuous areas of coated magnetic material form discrete separated islands on the device, with each discrete island functioning as a separate magnet. The discontinuous coating may, for example, be achieved by a discontinuous (e.g., pattern) coating process in which the magnetic material is coated in a manner that provides for discontinuous coatings of magnetic material. For example, the surfaces of the device may be masked such that a coating with magnetic material may not be attached to portions of the device surfaces.

In another approach, the coating may be applied as a substantially continuous layer in which discontinuities are formed after the continuous coating is applied. Discontinuities in such a continuous coating may be formed by any suitable technique, e.g., etching (chemical, ion beam, etc.), manipulation of the device (e.g., stretching, bending, crushing, expanding, rapid heating and cooling, etc.), mechanical abrasion, laser ablation, water jet etching, etc. Metallic coatings (e.g., nickel coatings) may be particularly amenable to cracking or fracturing in response to, e.g., mechanical/thermal stresses to provide a discontinuous magnetic coating.

Figure 4:
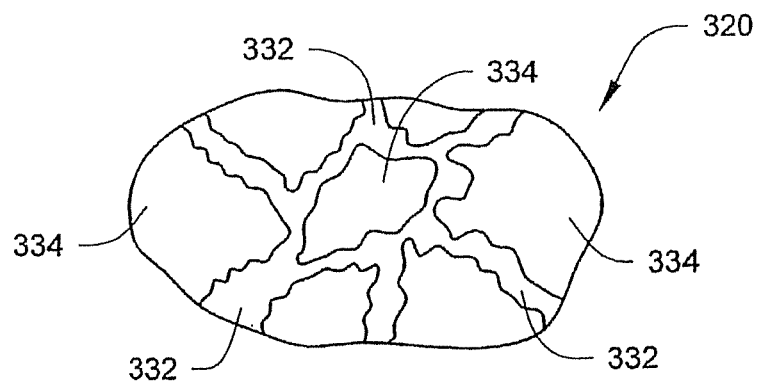
FIG. 4 is an enlarged view of a surface of another exemplary embodiment of a magnetic device according to the present invention including a discontinuous coating of magnetic material.

FIG. 4 is an enlarged view of a magnetic contact surface in one exemplary medical device that is formed by a surface 320 including a discontinuous coating of magnetic material in which fissures or fractures 332 are located between discrete islands 334 of magnetic material. Although the discrete islands 334 in the depicted embodiment are randomly-shaped (consistent with, e.g., a fractured or cracked magnetic coating), discontinuous magnetic coatings may alternatively have selected shapes (consistent with, e.g., pattern coating, etching, etc.) that are consistent with a more controlled etching process, coating process, etc. Additional examples of potentially suitable techniques for achieving discontinuous magnetic coatings on medical devices may be described in, e.g., WO 2004/093643 A2 (Levy et al.).

Although in some embodiments it may be preferred that the smaller magnets be distributed such that the magnetic fields are substantially uniformly distributed over the magnetic contact surfaces to be coated with the expectation that magnetic cells will be correspondingly uniformly attracted over the surfaces, such uniform distributions may not be required. For example, in some embodiments, the distribution and/or location of the magnetic particles and/or discrete islands of magnetic material may be manipulated to achieve a selected distribution of magnetic fields over the magnetic contact surfaces of the device. Such manipulation may be achieved by physical or electromagnetic forces during construction of the device or after construction in a post-construction process.

Another factor to potentially consider in connection with the present invention is that the size, shape, and/or magnetic field strength of the magnetic particles or discrete islands of magnetic material may be selected to achieve desired magnetic field properties in the devices of the present invention.

The distributed magnetic fields exhibited in devices of the present invention may preferably result in reduced field strength at any one location on the magnetic contact surfaces of the device as compared to other devices with fewer magnetic fields. For example, due to the distribution of the magnetic fields, it may be possible to achieve desired magnetic attraction of magnetic cells to magnetic contact surfaces of medical devices of the present invention with magnetic field strengths that are in the range of 10 Gauss or less, preferably 5 Gauss or less, or even 1 Gauss or less. It should, however, be understood that stronger magnetic fields may also be used in connection with the present invention.

It may be preferred that the magnetic domain size for applications in which magnetized cells are to be captured be 1 micrometer or larger. In embodiments in which a magnetized drug or sub-cellular particles (e.g., sub-cellular biological particles) are to be magnetically captured, the magnetic domain size may preferably be smaller, e.g., 1 nanometer or larger.

As discussed herein, it may be beneficial to provide vascular grafts with magnetic contact surfaces that can be magnetically coated according to the principles of the present invention. One approach to providing magnetic fields in a vascular graft may include weaving or knitting one or more magnetic strands into the structure of the vascular graft. The magnetic strands may be constructed of magnetic material (e.g., the strand could be a thin wire constructed of nickel or another magnetic material) or they may be constructed of a non-magnetic core with a magnetic coating located thereon (e.g., a polymeric core with a coating of magnetic material). Other constructions of magnetic strands may also be envisioned, e.g., a binder with magnetic particles dispersed throughout, etc. It may be preferred that magnetic material in the strands be coated in a biocompatible material as discussed herein.

Figure 5:
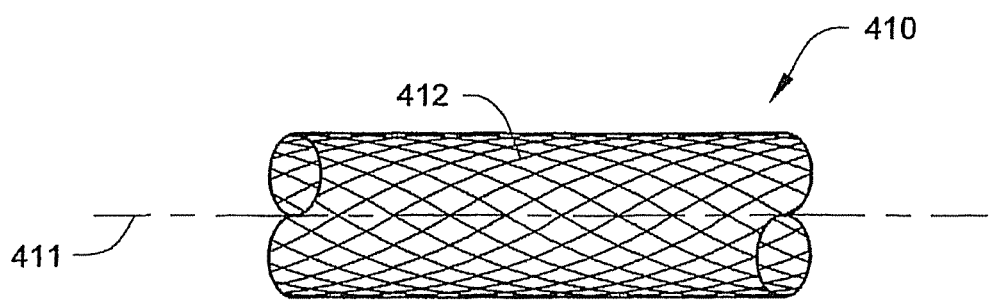
FIG. 5 is a side view of one exemplary graft in accordance with the present invention.

FIG. 5 depicts a vascular graft 410 in which at least one strand 412 within the fabric of the tubular graft 410 is constructed with magnetic material such that the graft 410 exhibits a magnetic field along its length (extending along longitudinal axis 411) as-well as about its periphery. Although magnetic strand 412 is depicted as being woven/knitted in a helical pattern, it will be understood that the magnetic strands provided in vascular grafts according to the present invention may be provided in any suitable pattern. An example of one alternative would be one or more magnetic strands extending in a substantially longitudinal direction (i.e., aligned with longitudinal axis 411) with the remainder of the graft fabric woven around the one or more magnetic strands. Another alternative could include multiple strands or fibers dispersed throughout the graft.

In addition, it should be understood that the size, spacing, and/or pattern in which the one or more magnetic strands may be provided can vary, i.e., the strands may be larger or more densely arranged within the fabric or less densely arranged within the fabric depending on the desired magnetic field pattern. In some instances, the density of the magnetic strands can change over selected areas of the graft 410, e.g., the density of the magnetic strands can increase in areas where an increased magnetic field is desired to potentially improve the magnetic coating process.

In still other variations, each magnetic strand could, itself, provide distributed magnetic fields along its length in accordance with the principles described herein. The distributed magnetic fields may be provided by, e.g., discrete magnetic particles distributed along the length or about the perimeter of the fiber as part of, e.g., the fiber core as discussed above in connection with FIG. 2, as a coating on each fiber as discussed in connection with FIG. 3, etc. The distributed magnetic fields could alternatively be provided or discrete islands of magnetic material located on a core such as, e.g., a discontinuous coating of magnetic material as discussed in connection with FIG. 4.

Figure 6:
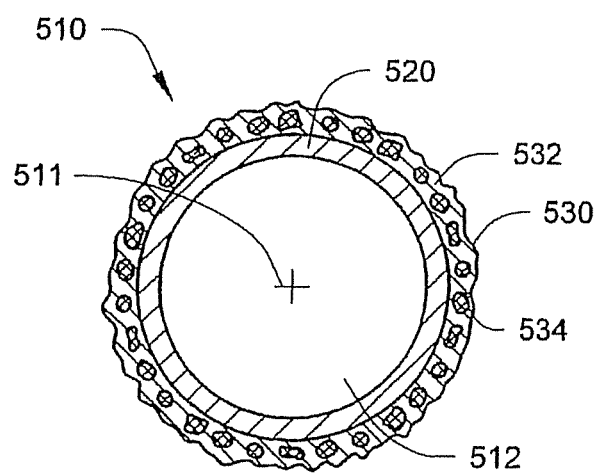
FIG. 6 is a cross-sectional view of an alternative exemplary graft manufacturing in accordance with the present invention.

FIG. 6 is a cross-sectional view of an alternative construction for a tubular vascular graft 510 that may be used in connection with magnetic coating as discussed herein. In the embodiment depicted in FIG. 6, a coating 530 is provided on the framework of the vascular graft 520. Where the vascular graft 520 is, itself, a flexible article, it may be preferred that the coating 530 also be flexible such that the composite structure of the coating 530 and the graft 520 exhibits the desired level of flexibility. The coating 530 may preferably include a non-magnetic binder 532 that contains magnetic particles 534 dispersed therein such that after coating 530 is in place on the graft 520, the magnetic particles 534 are distributed over the graft 520 to provide desired magnetic contact surfaces.

The binder 532 may in some instances be biodegradable, such that after attracting the desired magnetic cells to the graft 520, the coating 530 itself eventually degrades and is removed from the graft 520. The binder 532 may preferably be elastomeric in some embodiments. The binder 532 may be any suitable biocompatible material of synthetic or natural origin.

In some instances, the coating 530 may be located on the external or outer surfaces of the vascular graft 520 as depicted in FIG. 6. In other embodiments, the coating 530 (with its magnetic particles 534) may be located on the interior surface of the lumen 512 of the vascular graft 520. In still other embodiments, the coating 530 may be found in the interior and exterior surfaces of the graft 520. If the vascular graft 520 is constructed of a porous material (e.g., woven/nonwoven/knitted fabric, porous film, etc.), it may be preferred that the coating 530 permeate the vascular graft 520, such that it can be found on the interior and exterior surfaces of the graft 520 and/or bridge any openings in the fabric wall of the graft 520. In some embodiments, the coating 530 may also be entirely sandwiched or permeated within the layers of graft material such that the coating does not contact blood or tissue.

Figure 7:
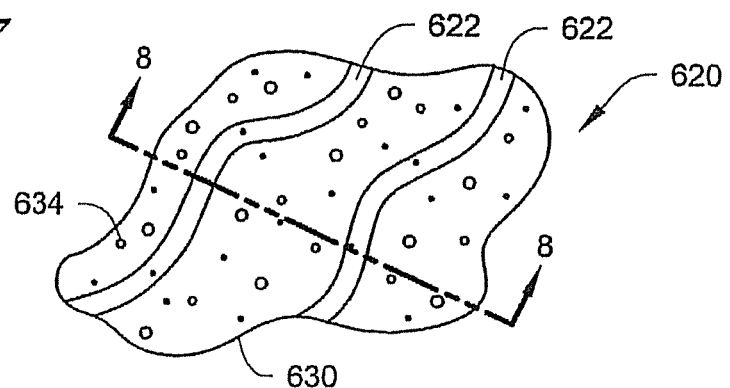
FIG. 7 is a plan view of a portion of one exemplary stent including a magnetic skin layer according to the present invention.
Figure 8:
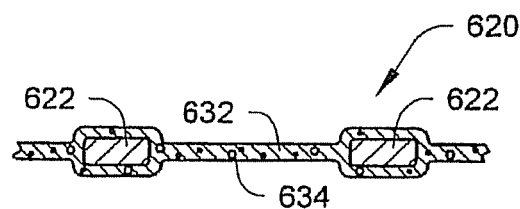
FIG. 8 is a cross-sectional view of the stent of FIG. 7 taken along line 8-8 in FIG. 7.

In another alternative, a non-magnetic coating or skin layer may be provided in connection with a stent or other article in which the spacing between structural elements is potentially larger than those found in a porous vascular graft or similar article. FIG. 7 depicts a plan view of a portion of one such medical device 620 that includes one or more struts 622 with a skin layer 630 bridging the gaps formed between portions of the struts 622. FIG. 8 is a cross-sectional view taken along line 8-8 in FIG. 7 to show that the non-magnetic binder 632 of the skin layer 630 may preferably encapsulate the struts 622 as well as extend between or bridge the gaps between struts 622. Such a skin layer 630 may function as a sleeve extending over the medical device 620. It may be preferred that the binder material used for the skin layer exhibit elastomeric properties such that the skin layer 630 can expand along with the underlying medical device 620 if the medical device is expandable (as are, e.g., many stents, etc.). Examples of some potentially useful materials for the non-magnetic binder may be described in, e.g., U.S. Pat. No. 6,375,787 B1 (Lukic) and U.S. Pat. No. 5,707,385 (Williams).

Figure 9:
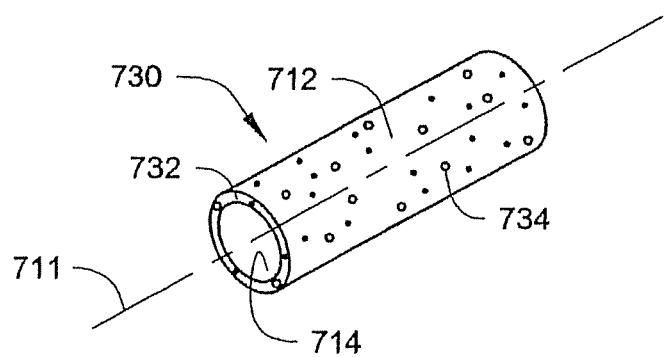
FIG. 9 is a perspective view of one exemplary magnetic sleeve according to the present invention.

FIG. 9 depicts another embodiment of a magnetic implantable device according to the present invention. The magnetic implantable device may preferably be in the form of a sleeve 730 having a generally tubular shape with an exterior surface 712 and an interior surface 714. The interior surface 714 may preferably define a lumen extending along the longitudinal axis 711 of the sleeve 730, with openings at both ends of the sleeve 730.

Unlike the coating 530 of FIG. 6 or the skin layer 630 of FIGS. 7 & 8, the sleeve 730 of FIG. 9 is provided as a separate and discrete article apart from any stent, graft, etc. One potential advantage to such a magnetic sleeve is the ability to use magnetic attraction in conjunction with a conventional medical device such as a stent, graft, etc.

Figure 10:
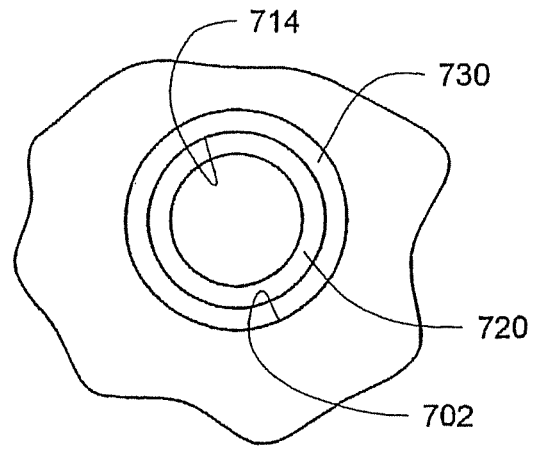
FIG. 10 is a view of the sleeve of FIG. 9 deployed within a body lumen.

The sleeve 730 may preferably be capable of delivery to an internal body location using another medical device to deliver the sleeve 730 such as, e.g., a stent, graft, balloon, etc. In some instances, the sleeve 730 may be located over the delivery device and, when deployed, be retained in place by the delivery device. As depicted in connection with FIG. 10, for example, the sleeve 730 may be held against the wall of a body lumen 702 by a stent 720, with the sleeve 730 located between the stent 720 and the wall of the body lumen 702.

Alternatively, the sleeve 730 could potentially be deployed within the interior of a stent, with the sleeve 730 attached to the stent by, e.g., adhesives, sutures, clamps, clips, etc. In such a deployment, the stent would be located between the exterior surface 712 of the sleeve 730 and a wall of a body lumen.

A similar deployment may be possible for systems in which the sleeve 730 is delivered using other tubular medical devices such as, e.g., vascular grafts. In such embodiments, the sleeve 730 may be located over the outside of the graft such that the interior surface 714 of the sleeve 730 faces the exterior surface of the graft. As a result, when the graft is deployed within a body lumen, the sleeve 730 is located between the vascular graft and the wall of the body lumen.

Alternatively, the sleeve 730 could potentially be deployed within the interior of the graft, with the sleeve 730 attached to the graft by, e.g., adhesives, sutures, clamps, clips, etc. In such a deployment, the graft would be located between the exterior surface 712 of the sleeve 730 and a wall of a body lumen.

The sleeve 730 may preferably be manufactured of a flexible material, such that the sleeve 730 can be delivered to an internal body lumen in a compact state unlike the expanded tubular structure depicted in FIG. 9. When in a selected body location, the sleeve 730 can be expanded to form the tubular structure depicted in FIG. 9. Flexibility in the sleeve 730 may also assist in delivery of the sleeve 730 if the pathway to the internal body lumen is tortuous. It may be preferred, for example, that the sleeve 730 be flexible such that it cannot maintain a self-supporting tubular shape as seen in FIG. 9 in the absence of some external support. In addition to flexibility, it may be preferred that the sleeve 730 exhibit elastomeric properties such that the sleeve 730 can be expanded (to at least some degree) without fracture or breakage.

The sleeve 730 may preferably be manufactured of a non-magnetic binder 732 in which magnetic particles 734 are distributed (as described, e.g., in connection with the coatings of FIG. 3). In the case of a sleeve 730, it may be preferred that the non-magnetic binder 732 be in the form of a polymeric film, although any suitable non-magnetic binder 732 may be used so long as the material is capable of forming a usable sleeve in which magnetic particles 734 may be located.

Magnetic particles 734 may preferably be randomly distributed throughout the body of the sleeve 730. Alternatively, the magnetic particles 734 located within the non-magnetic binder 732 may be provided in a selected distribution (e.g., a uniform pattern, anon-uniform pattern, etc.). The magnetic particles 734 used in a sleeve 730 may preferably be permanently magnetized or they may be formed of materials that may be temporarily magnetized as discussed herein.

It may be preferred that the sleeve 730 be constructed of biodegradable materials that, over time, will degrade or erode as is known in the art of implantable medical devices. Alternatively, the sleeve 730 may retain its integrity after implantation.

The sleeve 730 may also preferably be either porous (e.g., permeable to liquids) or nonporous. Porous sleeves 730 may be useful in allowing diffusion of water, nutrients, etc. through the membrane to tissue against which the sleeve 730 is located.

The wall thickness of the sleeve 730, i.e., the radial distance between the exterior surface 712 and the inner surface 714, may vary depending on the materials used, the location at which the sleeve 730 is to be implanted, etc. It may be preferred, for example, that the sleeves have a wall thickness of 1 millimeter or more. At the upper end, it may be preferred that the sleeves have a wall thickness of 5 mm or less in some embodiments.

Although depicted as having a wall that is constructed of a single layer of binder 732 in which magnetic particles 734 are distributed, the sleeve 730 may be constructed with a multi-layer wall in which, e.g., the different layers may preferably provide different functionalities.

Figure 11:
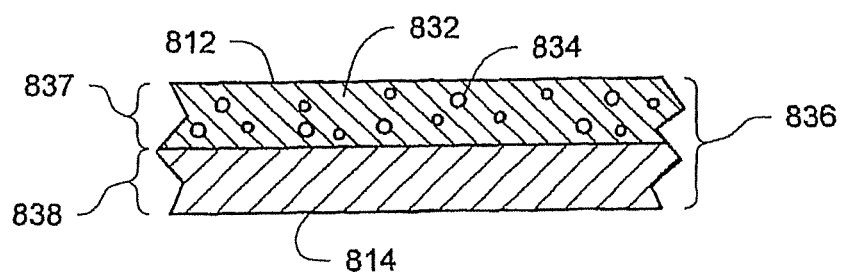
FIG. 11 is a cross-sectional view of one exemplary multilayer construction that may be used in connection with the present invention.

An example of one such structure is depicted in connection with FIG. 11 in which a portion of a sleeve wall 836 is depicted. The sleeve wall 836 may preferably include an exterior surface 812 and an interior surface 814 as discussed herein. In between the exterior surface 812 and the interior surface 814, the wall 836 may preferably include two (or more) layers 837 and 838. Layer 837 may, for example preferably include magnetic particles 834 distributed within a non-magnetic binder 832, with the magnetic particles 834 providing the desired magnetic attraction. Layer 838 may preferably provide a different functionality, e.g., layer 838 may be a drug-eluting layer, etc. In some instances, the different functionality may be structural, i.e., layer 838 may preferably assist in maintaining the structural integrity of the sleeve wall 836.

In a multilayer sleeve wall 836, some or all of the layers may be biodegradable. Further, if one or more of the layers are biodegradable, the different biodegradable layers may biodegrade at the same or different rates when implanted.

Although described in connection with a stent or a graft, the magnetic sleeves of the present invention may alternatively be provided in connection any other suitable implantable intravascular or intraluminal medical devices. For example, the magnetic sleeves may be deployed within a body lumen, luminal organ, etc. in the absence of a stent or a graft. Examples of other potential medical devices with which a magnetic sleeve according to the present invention may potentially be used include, but are not limited to: prostheses for other biologic conduits (e.g., neurologic, gastrointestinal, renal, endocrine, pulmonary, urologic, etc.), heart valves, artificial hearts, left ventricular assist devices, coronary device leads (for, e.g., pacemakers, defibrillators, etc.), arterio-veinous fistulas for dialysis, etc. In other applications, coils used to embolize and occlude aneurysmal sacs in blood vessels or to occlude blood vessels supplying malignant tumors may be used in connection with magnetic sleeves to expedite healing in aneurysms or the occlusion of vessels to tumors. Devices for treating endovascular leaks (holes/ruptures in blood vessels, valves or heart chambers) may also be used with magnetic sleeves to facilitate healing and reduce thrombosis. Magnetic devices may also be used to localize cells for treating malignancies in, e.g., organs. Magnetic devices and cells (that, e.g., produce therapeutic agents) may also be placed in blood vessels that supply a tumor.

In the absence of a stent, graft, etc. to retain the sleeve in a selected location, it may be preferred, e.g., that the sleeve be retained in place by any suitable technique or combination of techniques. For example, some sleeves of the present invention may be retained in place using receptor-ligand attachments, mechanical anchors (e.g., sutures, staples, tissue anchors, etc.), biologic attachments, chemical attachment (e.g., adhesives, etc.), RF tissue welding, electrical charges, magnetic attractive forces, hydrogen bonding, etc. Deployment of a magnetic sleeve according to the present invention in the absence of a stent or vascular graft may be accomplished by any suitable apparatus and/or technique, e.g., balloons, surgically, etc.

Figure 12:
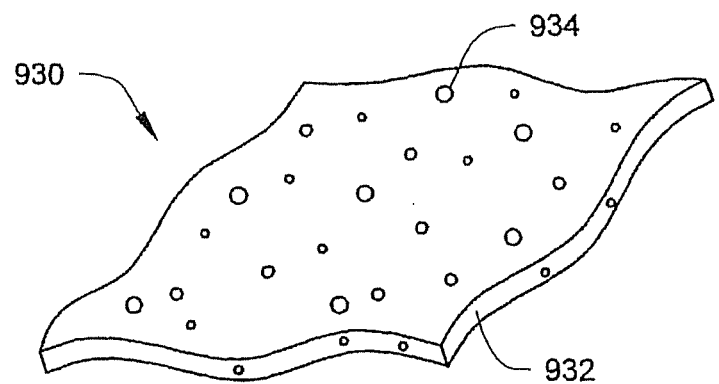
FIG. 12 is a perspective view of one exemplary magnetic sheet according to the present invention.

Although described herein in terms of tubular sleeves, it should be understood that the tubular sleeves may be formed as a true sleeve or as a sheet that is coiled to form a tubular shape. FIG. 12, for example, depicts a magnetic sheet 930 that may be coiled to form a tubular structure in accordance with the present invention. The magnetic sheet 930 may preferably be constructed with magnetic particles 934 in a non-magnetic binder 932. The variations described above with respect to the tubular magnetic sleeves may also apply to the sheet 930, e.g., compositions, thickness, magnetic particles, biodegradability, permeability/impermeability, flexibility, etc.

A magnetic sheet 930 may be used in a variety of applications in which a tubular structure is not necessary—both implanted within the body or on the surface of the body. Flexible sheets may be preferred if they are capable of closely conforming to a surface on which they are located. Examples of potential uses for magnetic sheets may include, e.g., for the treatment of burns or other plastic surgery/cosmetic cell-based applications where magnetic attraction can be used to enhance treatment.

Magnetic Cells

The present invention includes devices with magnetic contact surfaces that are coated with magnetic cells attracted to and retained on the magnetic contact surfaces by magnetic forces. The present invention also includes methods of coating the magnetic contact surfaces with magnetic cells.

The cells that are used as magnetic cells in connection with the present invention may include, e.g., any biologic cell that is capable of itself exhibiting a magnetic charge, being modified to incorporate one or more particles that include a magnetic charge, or that can be attached to a particle or cell that includes a magnetic charge. The magnetic cells of the present invention may be, e.g., endothelial cells, when used in blood contacting medical devices. In addition, the magnetic cells may be, e.g., ectoderm-, mesoderm-, endoderm-derived cells. Additionally, any stem or mature cell originating from various primitive cell layers in animals or humans may be modified to become magnetic cells useful in connection with the present invention.

In other variations, the magnetic cells may be engineered to carry new genes that may secrete products capable of treating disease, e.g., heart failure, coronary artery disease, cancer, etc.

A variety of techniques for modification of cells such that the cells become magnetic cells subject to magnetic attraction are known. Magnetic particles may be incorporated into the cell or attached to the cell surface by procedures known to those skilled in the art. In certain embodiments, magnetic particles may be fed to the target cells (Moller et al. (1997) J Aerosol Med 10:173-186; Violante (1990) Acta Radiol Suppl 374: 153-156) or temporary pores may be created in the cell membrane of the target cell by electroporation (Moroz et al. (1997) Biophys J 72:2211-6; Zhelev et al. (1993) Biochim Biophys Acta. 1147(1):89-104; Neumann et al. (1998) Faraday Discussions 111:111-125). In other embodiments, magnetic particles may be attached to the cell surface via antibody binding to cell membrane receptors or through chemical conjugation of the magnetic particle to the cell membrane (Yin et al. (1997) Blood 90: 5002-5012; Buckley et al. ABL 1998 Jun. 30-32).

In certain embodiments, cells may be magnetically modified or labeled by intravenous injection of magnetic particles which are conjugated to molecules which in turn will attach to the surface of the cells to be recruited to the surface. One such example constitutes the antibody-mediated binding of magnetic particles to the CD133 or CD34 protein found on the surface of several progenitor cell types. These cells may be endothelial progenitor cells or mature endothelial cells which may or may not have been genetically modified to express or produce an agent with an inhibitive effect on smooth muscle cell proliferation.

Para- or ferromagnetic particles may be enclosed in lipid membrane vesicles (liposomes) associated with the targeted cell or within a polymer matrix of micro- and nanoparticles attached to the cell of interest. Alternatively, the magnetic particles may be conjugated to the cellular surface of the targeted cell to constitute part of the cellular membrane. The cells may be recruited from the bloodstream to the magnetically charged prosthesis by magnetic attraction.

The strength of magnetic attraction typically depends on the magnetic properties of the particles utilized to modify the cells to be recruited to the magnetic contact surface, as well as the strength of the magnetic field emanating from the magnetic contact surface, and the gradient of this field where both the field and its gradient will vary with location. The magnetic properties of the particle depend on the chemical composition of the particle as well as its magnetization state. The properties of the magnetic field depend on surface and body geometry, the chemical composition and magnetic history of the device. Once attracted to the magnetic contact surface, the cells are preferably retained on the surface and, in certain embodiments, cell adhesion may induce cellular spreading and differentiation over the magnetic contact surface(s) as well as other surfaces of the medical device.

In other embodiments, increasing cell affinity to magnetic contact surfaces may include incorporating magnetic particles into the cells through fusion of vesicles to the cells. A vesicle defines a volume enclosed by a membrane. This membrane may include proteins, lipids, polymers, block-copolymers, or a mixture thereof. When such a vesicle fuses with a cell, the vesicle volume becomes part of the cell plasma and the vesicle's contents are released into the cell interior. If the vesicle is loaded with magnetic particles during vesicle formation, fusion of the vesicles with the cells results in incorporation of these magnetic particles into the cells' interiors.

Another technique for incorporating magnetically sensitive particles into target cells is by endocytosis. For this purpose, magnetic particles are fed to cells with endocytotic capabilities. Upon contact with a particle, cells, which may be stimulated to do so, will engulf the particle by adhering their membrane to the particle, followed by increasing the area of adherence until the entire particle is enclosed by a membrane section of the cell. After enclosure, the particle is incorporated into the cell interior by virtue of invagination of the membrane enclosed particle. In yet another embodiment, small magnetic particles with a diameter between, e.g., 50 nanometers (nm) and 250 nm may be brought into the target cell by creating temporary pores in the cell membrane through electric field exposure (i.e. electroporation). These standard techniques and others useful in the methods of the invention may be described by the following references, Moller et al. (1997); J Aerosol Med 10:173-186; Violante (1990) Acta Radiol Suppl 374: 153-156); Moroz et al. (1997) Biophys J. 72:2211-6; Zhelev et al. (1993) Biochim Biophys Acta. 1147(1):89-104.

Modification of cell magnetic properties in certain embodiments may include attaching magnetically sensitive particles, such as ferromagnetic or paramagnetic particles (including, but not limited to, e.g., ferrite, samarium cobalt, neodymium boron) to the surface of the cells. This may be achieved by modifying the surface of these particles to have affinity for the membrane of the cell. This affinity may be established by attaching ligand molecules to the magnetic particle. The magnetic particle can then bind via the ligand to an appropriate cell surface molecule present on the outer surface of the cell. The binding of magnetic particles to the cell membrane may also be achieved by reacting the magnetic particle (or a particle-encapsulating polymer matrix) to molecular groups typically found at cell membranes, including groups such as amine or thiol or hydroxyl groups, through chemically reactive groups presented at the particle or matrix surface.

In other embodiments, the cell can be modified to be magnetically charged by encapsulating the magnetic particle within or attached onto a polymeric matrix that is modified to have an affinity to the cell membrane. The surface of magnetic particle and/or the polymeric matrix may include proteins or peptide sequences, e.g., such as RGD peptides, which provide sites of attachment for cell surface integrins.

Standard protocols (as described by, e.g., Kemshead et al. (1985) Mol Cell Biochem 67:11-18) have been utilized to magnetically modify target cells of the invention. The size of these particles is dependent on target cell type as well as the desired strength of the magnetic attraction. Magnetic particles that may be useful in the invention may have a diameter which ranges from 50 nm or higher, in some instances 100 nm or higher. At the upper end of the range, the magnetic particles may have a diameter of 5 micrometers (μm) or less, or in some instances 1 μm or less.

Coating Magnetic Contact Surfaces with Magnetic Cells

The methods of the present invention involve magnetically attracting and retaining magnetic cells on magnetic contact surfaces of medical devices. The coating is preferably accomplished by locating the medical device in a carrier liquid containing the magnetic cells. The magnetic contact surfaces of the medical device are located within the carrier liquid such that the magnetic cells within the carrier liquid can be magnetically attracted to and retained on the magnetic contact surfaces.

The coating process be accomplished in vivo or ex vivo (e.g., in vitro), wherein the magnetic contact surfaces of the medical device can be located within a carrier liquid containing concentrations of magnetic cells that are significantly higher than, e.g., the concentration of magnetic cells in the bloodstream in an in vivo recruitment process such as that described in, e.g., U.S. Patent Application Publication No. US 2003/0082148 A1 (Ludwig et al.).

The carrier liquid in which the magnetic cells are provided may take a variety of forms, although it may preferably be a biologically compatible liquid. Examples of some suitable biologically compatible carrier liquids include, but are not limited to, solutions of 0.9% normal saline, Ringer's solution, various tissue culture media, serum, plasma, whole blood, etc. The solutions may also include one or more of, e.g., growth factors, hormones and other biologic or synthetic materials.

Regardless of the composition of the carrier liquid, the concentration of magnetic cells in the carrier liquid may preferably be significant. For example, the concentration of magnetic cells may be, e.g., 1000 magnetic cells per milliliter (ml) or higher, in some instances 10,000/ml or higher, and in still other instances 100,000/ml or higher, or even 1,000,000/ml or higher.

It may be preferred, in some embodiments, that the magnetic cells that are magnetically attracted to and retained on the implantable medical device are retained on the implantable medical device in the absence of ligand binding, fibronectin, antibodies, proteins, etc. Essentially, any biocompatible device surface may be used for direct cell to device surface contact without requiring surface modification. In other words, it may be preferred that magnetic force is the primary force involved in both attracting and retaining the magnetic cells on the magnetic contact surfaces of the medical devices.

In other embodiments, the methods of the present invention may be characterized on the basis of the time required to magnetically coat the medical devices. For example, the methods may involve locating the medical device to be coated in the carrier liquid containing the magnetic cells for a period of one hour or less to coat the magnetic coating surfaces to a desired level. In some instances, the coating may be accomplished in less time, for example, in some instances, it may be possible to coat the magnetic coating surfaces by locating the medical device in the carrier liquid for a period of 30 minutes or less, 15 minutes or less, 10 minutes or less, etc.

The methods of the present invention may also be characterized on the basis of coverage of the magnetic contact surfaces of the medical devices (for either in vivo or in vitro coating methods). For example, it may be preferred that, for the magnetic contact surface of the medical device in contact with the carrier liquid containing the magnetic cells, 25% or more of the magnetic contact surface in contact with the carrier liquid is coated by the magnetic cells. In some cases, it may be preferred that 50% or more of the magnetic contact surface located in the carrier liquid be coated by the magnetic cells, and in other cases it may be preferred that substantially all of the magnetic contact surfaces located in the carrier liquid be coated by the magnetic cells. In addition, these coating levels, e.g., coating 25% or more of the magnetic contact surface in contact with the carrier liquid with the magnetic cells may preferably be performed within time periods of 30 minutes or less, 15 minutes or less, or even 10 minutes or less.

The coating levels described in the preceding paragraph may, in some instances, be obtained before the medical device is used, e.g., implanted in a body. Furthermore, the methods of the present invention may include inspection of the magnetic contact surfaces to determine if the desired coating level is achieved before using (e.g., implanting, etc.) the medical device. If the inspection reveals that the coating is not acceptable, the medical device can be returned to a carrier liquid containing the desired magnetic cells to improve the coating level.

In some embodiments, the methods of the present invention may involve coating only a portion of the magnetic contact surfaces of the medical device with magnetic cells. Such selective coating of the magnetic surfaces may be performed by, e.g., contacting only selected portions of the magnetic contact surfaces with the carrier liquid containing the magnetic cells.

The methods of the present invention may, in some instances, involve contacting all of the magnetic contact surfaces on a medical device with the carrier liquid containing the magnetic cells, such that, for example, the magnetic cells can be magnetically attracted to and retained on all of the magnetic contact surfaces. Such a method, may, for example, involve immersing the entire medical device in the carrier liquid containing the magnetic cells.

Because the medical devices of the present invention may be constructed of materials that are not permanently magnetic, the methods of the present invention may, in some instances, involve magnetizing at least a portion of the medical device to form the magnetic contact surfaces that will be coated when the medical device is located in a carrier liquid containing the magnetic cells. Magnetic fields may be induced by any suitable technique, e.g., locating the medical device in an electric field, locating the medical device in a magnetic field, etc.

Figure 13:
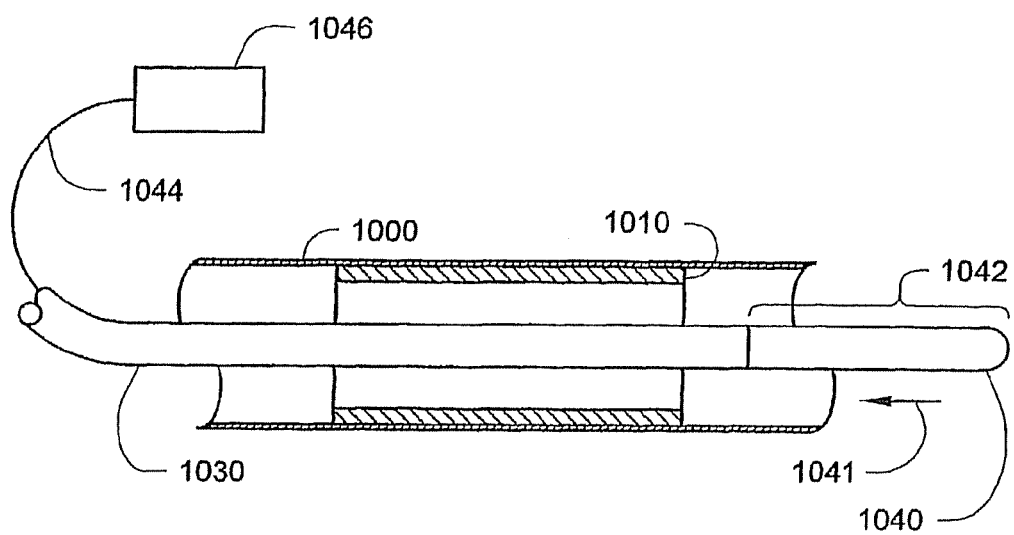
FIG. 13 is a schematic diagram of one apparatus and method for magnetizing an implanted medical device in vivo.

One potential apparatus and method of magnetizing a magnetizable medical device is depicted in FIG. 13. The medical device 1010 is in the form of a stent deployed within a vessel 1000. The medical device 1010 preferably includes one or inure magnetizable materials such that one or more magnetic contact surfaces can be provided on the medical device 1010.

If the magnetizable materials do not inherently exhibit magnetic fields of sufficient strength to attract magnetic biologic cells as discussed herein, it may be advantageous to expose the magnetizable materials to a magnetic field or electric field after implantation within a subject. The depicted apparatus includes a medical grade catheter 1030 that includes a magnetic field generator 1040 adapted for deployment through the lumen formed within the stent 1010. In other embodiments, the medical device may or may not include a lumen through which the magnetic field generator can pass. In such embodiments, it may be sufficient that the magnetic field generator pass near the implanted medical device.

As used herein, a "medical grade catheter" is a catheter that is constructed such that it may be inserted into the body of a subject. Preferably, a medical grade catheter is capable of being sterilized. The magnetic field generator 1040 may, e.g., occupy a section 1042 of the catheter 1030 proximate the distal end thereof as seen in FIG. 13.

It is typically preferred that the magnetic field generator 1040 provide a magnetic and/or electric field sufficient to induce the magnetic materials within the medical device 1010 to exhibit a magnetic field (if they are not permanently magnetized). The induced magnetism in the medical device 1010 is preferably strong enough to magnetically attract biologic cells as discussed herein when the magnetic field generator 1040 is advanced through the medical device 1010 and/or drawn back through the medical device 1010 in, e.g., the direction of the arrow 1041. In some embodiments, the magnetic field generator may preferably reside in or near the medical device 1010 for a selected dwell time.

In some embodiments, the magnetic field generator 1040 may be in the form of one or more magnets. In other embodiments, the magnetic field generator may be in the form of one or more electric coils connected to a power source 1046 by an electrical lead 1044 extending along the length of the catheter 1030 and providing electrical energy to the coil. The power source 1046 may preferably be located outside of the body of the subject in which the medical device 1010 is implanted. In either form, the magnetic field generator 1040 is preferably capable of inducing magnetization in magnetizable materials located in close proximity to the magnetic field generator 1040.

The catheter 1030 and its magnetic field generator 1040 may also serve a function other than magnetizing the medical device 1010. In some embodiments, the catheter 1030 may be used to degauss or demagnetize an implanted medical device 1010. Demagnetization may be desired after the magnetically attracted biologic cells have formed other attachments to the medical device 1010 (e.g., after 24-48 hours). If the magnetic field generator 1040 is configured as a degaussing element to degauss a magnetic medical device, then in vivo degaussing of a medical device may be performed.

If degaussing is performed as a part of the present invention, it should be understood that the degaussing may not necessarily eliminate the magnetic fields exhibited by a medical device. Rather, the degaussing may simply reduce the magnetic field strength below the magnetic field strength exhibited by the magnetic contact surfaces before the degaussing. In some instances, it may be desirable that the magnetic field strength be reduced as a result of the degaussing by, e.g., 50% or more.

It should be understood that although the catheter 1030 and its magnetic field generator 640 are depicted in connection with a medical device 1010 in the form of a stent, the in vivo magnetization of an implanted medical device may be performed with virtually any implanted medical device. Furthermore, the magnetic field generator need not be inserted through an implanted medical device. Rather, the magnetic field generator need only be located close enough to the implanted medical device to induce the desired magnetization in the medical device.

In some instances, the magnetic field generator may not even need to be advanced to an in vivo location to magnetize an implanted medical device. For example, a magnetic field generator may be located outside of the subject's body in a location near enough to the implanted medical device to induce magnetization of the magnetic materials in the medical device. In such an application, degaussing may also be performed using an external degaussing unit located proximate the implanted medical device.

Figure 14:
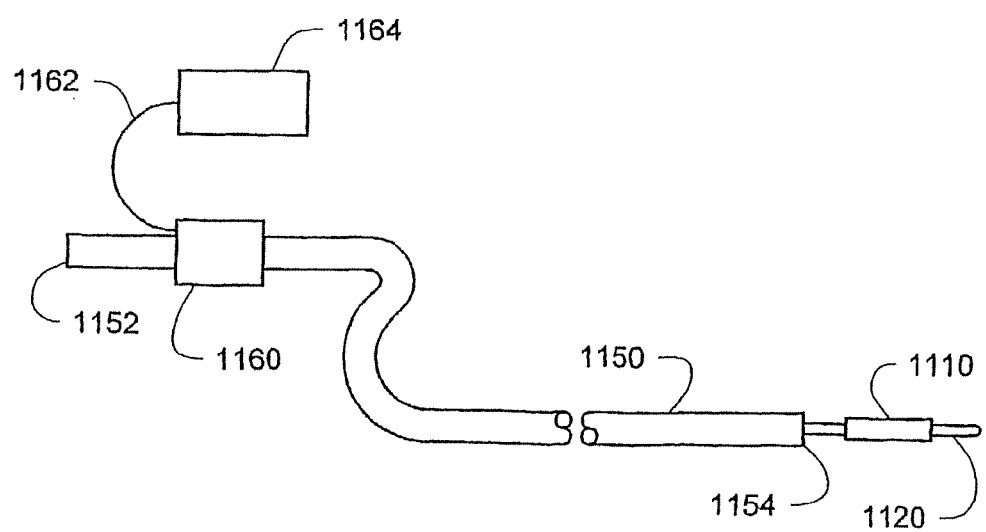
FIG. 14 is a schematic diagram of one apparatus and method for magnetizing an implantable medical device during the implantation process.

The apparatus depicted in FIG. 14 is one example of another technique for magnetizing a medical device for in vivo magnetic coating according to the principles of the present invention. The apparatus includes an elongated body 1150 such as, e.g., a guide catheter, sheath, etc. that preferably includes at least one lumen extending from a proximal end 1152 to a distal end 1154. The body 1150 may preferably be adapted to assist in the delivery of a medical device 1110 to an internal body location. The medical device 1110 may preferably be carried on, e.g., a catheter 1120 as seen in FIG. 14.

The apparatus of FIG. 14 is adapted to magnetize a medical device during the implantation process. To do so, the apparatus preferably includes a magnetic field generator 1160 located proximate the proximal end 1152 of the body 1150. It may be preferred that the magnetic field generator 1160 be positioned such that it does not enter the subject's body as does the distal end 1154 of the body 1150. During advancement through the body 1150, it is preferred that the medical device 1110 pass by the magnetic field generator 1160 or through an opening formed within the magnetic field generator 1160 such that a magnetic field is induced in the medical device 1110.

In some embodiments, the magnetic field generator 1160 may be in the form of one or more magnets. In other embodiments, the magnetic field generator 1160 may be in the form of one or more electric coils connected to a power source 1164 by a lead 1162. In either form, the magnetic field generator 1160 is preferably capable of inducing magnetization in magnetizable materials located in close proximity to the magnetic field generator 1160.

Although the coating of medical devices with magnetic cells may be accomplished in vitro, it may be preferred that the medical devices be magnetically coated after placement in a desired location within the body, i.e., in vivo. To provide sufficient numbers of magnetic cells to adequately coat the magnetic contact surfaces of a medical device, however, it may be desirable to provide the medical device within a defined volume in vivo. A carrier liquid containing the selected magnetic cells can then be introduced into the defined volume, with the magnetic cells being magnetically attracted to and retained on the magnetic contact surfaces of the medical device. The defined volume may be provided in a manner that excludes other bodily fluids, such as, e.g., blood, cerebrospinal fluid, bile, etc. Such in vivo magnetic coating may preferably be accomplished after magnetization of the implanted medical device before implantation, during implantation, and/or after implantation as described herein.

In some instances, the defined volume into which the carrier liquid is introduced may be naturally occurring fluids such as, e.g., blood, bile, saliva, urine, cerebrospinal fluid and fluids in the gastrointestinal tract, peritoneal cavity, pleural space, pericardial sac and synovial fluid in joint cavities, etc.

Figure 15:
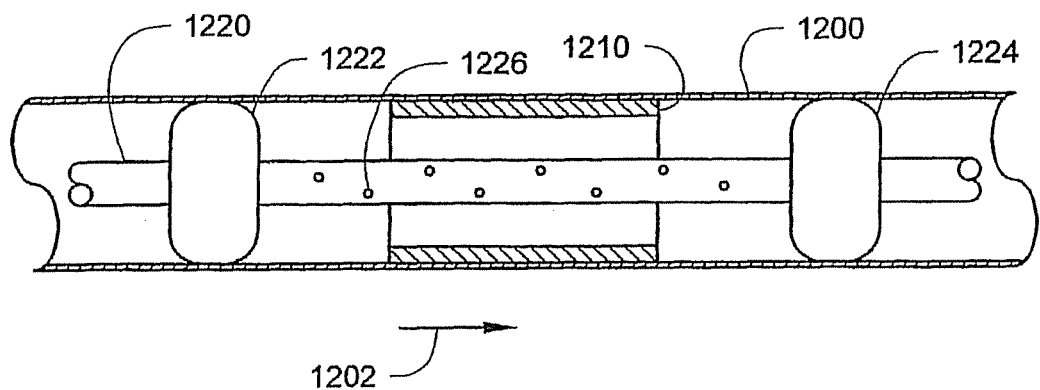
FIG. 15 is a schematic diagram of one method for magnetically coating an implanted medical device in vivo.

In other instances, it may be preferable to create the defined volume in vivo. FIG. 15 is a schematic diagram of one technique that may be used to create a defined volume in vivo into which the carrier liquid containing magnetic cells may be introduced. The depicted technique may be performed in a lumen 1200 such as, e.g., blood vessel, using a catheter 1220 that can be guided into position by any suitable technique, e.g., using a guidewire.

In the depicted embodiment, a stent 1210 is in position within the vessel 1200 before the catheter 1220 is positioned therein. Alternatively, the catheter 1220 may be used to deliver and deploy the stent 1210 if, e.g., the catheter 1220 includes a deployment balloon or other structure for deploying the stent 1210 in the vessel 1200.

With the stent 1210 in position, the catheter 1220 is positioned such that a first seal 1222 is located upstream from the stent 1210 and a second seal 1224 is located downstream from the stent 1210. In the depicted embodiment, upstream and downstream positions are relative to arrow 1202 which is indicative of blood flow through the vessel 1200. Once in position, the seals 1222 and 1224 are deployed to enclose a defined volume between the proximal seal 1222 and the distal seal 1224. The seals 1222 and 1224 may be, e.g., balloons that can be inflated through one or more lumens in the catheter 1220.

With the seals 1222 and 1224 in operation, a carrier liquid with magnetic cells located therein can be delivered to the defined volume located in vessel 1200 between seals 1222 and 1224. In the depicted embodiment, the carrier liquid with magnetic cells can be delivered through a lumen located in catheter 1220, the carrier liquid and magnetic cells entering the defined volume through openings 1226 in the catheter 1220. Many other fluid delivery structures will be known to those skilled in the art.

If vessel 1200 is a blood vessel and it is desirable to allow the carrier liquid and magnetic cells reside within the defined volume enclosed by seals 1222 and 1224 for a period of time longer than the flow of blood through vessel 1200 can be terminated, the catheter 1220 may be a perfusion catheter, i.e., a catheter that includes a lumen capable of passing blood from the upstream side of the first seal 1222 to a point past the downstream side of the second seal 1224.

After the carrier liquid and magnetic cells have resided in the defined volume for a sufficient time to magnetically coat the stent 1210 with the magnetic cells, the seals 1222 and 1224 can be opened (e.g., deflated if they are provided in the form of balloons) such that stent 1210 is no longer contained within a defined volume. If desired, the carrier liquid may be removed from the defined volume before the seals are opened.

In one variation of the device and method described with respect to FIG. 15, it should be understood that the first seal 1222 may be optional. In other words, only the second seal 1224 may be needed if the vessel 1200 is used for the passage of a fluid such as blood on a continuous basis. Rather, by closing the downstream seal 1224 and providing carrier liquid containing the desired magnetic cells at a pressure greater than, e.g., the blood pressure at the location of the stent 1210, the carrier liquid and magnetic cells may be entrapped within the volume defined by the downstream seal 1224 and the fluid (e.g., blood) flowing against the seal 1224. In some instances, it may be possible to deliver the carrier liquid on the upstream side of the seal 1224 using, e.g., the lumen of guide catheter used to deliver the device depicted in FIG. 15. In some instances it may be possible to deliver the carrier liquid downstream of seal 1222 (e.g., without deploying seal 1224 or using a device that includes only one seal). The lack of blood flow caused by occlusion due to seal 1222 may preferably allow the delivered liquid to remain downstream of seal 1222 for period of time sufficient to magnetically coat the stent 1210.

Examples of devices capable of operating as described in connection with FIG. 15 may be found in, e.g., U.S. Pat. No. 6,575,932 (O'Brien et al.); U.S. Pat. No. 5,558,642 (Schweich, Jr. et al.); U.S. Pat. No. 5,135,484 (Wright), etc.

In some instances, it may be possible, or even desirable to magnetically coat a magnetic medical device in vitro. For example, the present invention may be in the form of a kit that includes a flexible tubular conduit designed for placement as, e.g., a synthetic blood vessel or an arterio-veinous graft for dialysis. Such a conduit may preferably include a lumen defined by natural or synthetic biocompatible fibrous fabrics with magnetized filaments woven into the fabric to attract and retain magnetic cells to the interior surfaces of the lumen. Such a conduit may be filled with a carrier liquid and magnetic cells in vitro. The in vitro residence time of the carrier liquid may be extended until the magnetic cells are established on the interior surfaces of the lumen, after which the conduit may be surgically implanted as, e.g., a bypass graft or an arterio-veinous fistula.

Kits of the Present Invention

The various components and materials described herein may be assembled into different kits to assist practitioners in practicing the methods of the present invention. These kits may preferably be contained within a single, sterilizable package to further enhance the ease of use by practitioners. Some exemplary embodiments of such kits may be described below.

One embodiment of a potential kit according to the present invention is a kit for magnetically coating a medical device in vivo. Such a kit may include, e.g., an implantable medical device with a magnetic contact surface and means for enclosing a defined volume in vivo in which the implantable medical device is located when implanted. The means for enclosing a defined volume may include any of the structures described herein and equivalents thereof. The implantable medical device in the kit may be selected from, e.g., the group consisting of a magnetic sleeve, magnetic sheet, blood vessel stent, vascular graft, prosthesis for any biologic conduit; heart valve, artificial heart, left ventricular assist device, and electronic leads. The means for enclosing a defined volume in vivo may be adapted for enclosing the defined volume in a biologic conduit such as, e.g., a blood vessel.

Another embodiment of a kit according to the present invention may include, a kit for magnetically coating a medical device in vivo. Such a kit may include, e.g., an implantable medical device with a magnetic contact surface and a catheter for creating a defined volume in a biologic conduit in vivo. The catheter may include at least one seal capable of closing the biologic conduit when deployed within the conduit, a carrier liquid lumen extending from a proximal end of the catheter to a location proximate the at least one seal, and an opening in the carrier liquid lumen proximate the at least one seal, wherein carrier liquid in the carrier liquid lumen is capable of exiting the catheter proximate the seal such that the carrier liquid is located within the defined volume. In such a kit, the at least one seal may include a pair of seals such that the defined volume is enclosed by the pair of seals when the pair of seals are deployed within the biologic conduit. Each seal may include an inflatable balloon, and the catheter may include one or more inflation lumens extending from the proximal end of the catheter to the seals. The components of the kit may be adapted for deployment within a biologic conduit in the form of blood vessel.

Another embodiment of a kit that may be provided in connection with the present invention is a kit for magnetizing a medical device in vivo. The kit may include an implantable medical device comprising magnetic material and a magnetizing apparatus for magnetizing the magnetic material of the implantable medical device in vivo. The magnetizing apparatus may include a medical grade catheter with a proximal end and a distal end. A magnetic field generator may be operably attached to the catheter, wherein the magnetic field generator is located proximate the distal end of the catheter. The magnetic field generator may preferably be sized such that it can be advanced through a biologic conduit of a subject. The implantable medical device may be selected from the group consisting of a blood vessel stent, vascular graft, prosthesis for any biologic conduit; heart valve, artificial heart, left ventricular assist device, and electronic leads. The magnetic field generator may include a permanent magnet. Alternatively, the magnetic field generator may include an electric coil and an electrical lead attached to the electric coil, the electrical lead extending towards the proximal end of the catheter, whereby electrical energy can be delivered to the electric coil through the electrical lead. In some embodiments, the electrical lead may extend to the proximal end of the catheter. The kit may also include a power source for delivering electrical energy to the electric coil. In still other embodiments, the kit may include (as described herein) means for enclosing a defined volume in vivo in which the implantable medical device is located when implanted.

Still another embodiment of a kit according to the present invention may include a kit for magnetizing a medical device, wherein the kit includes an implantable medical device comprising magnetic material and a magnetizing apparatus for magnetizing an implantable medical device. The magnetizing apparatus may include an elongated body with a proximal end and a distal end, wherein the elongated body includes a lumen extending from the proximal end to the distal end. The magnetizing apparatus may also include a magnetic field generator located proximate the proximal end of the elongated body, wherein a medical device advanced through the lumen from the proximal end towards the distal end passes through a magnetic field generated by the magnetic field generator. The magnetic field generator may include a permanent magnet. In some embodiments, the Magnetic field generator includes an electric coil and an electrical lead attached to the electric coil, whereby electrical energy can be delivered to the electric coil through the electrical lead. The kit may also include a power source for delivering electrical energy to the electric coil. The elongated body may preferably be in the form of a guide catheter adapted for insertion into a biologic conduit such as, e.g., a blood vessel. The elongated body may alternatively be in the form of an introducer sheath.

The various kits of the present invention may also include means for associating a magnetic charge with a plurality of biologic cells as described herein. The kit may also include a carrier liquid for delivery to the enclosed defined volume in vivo. The carrier liquid may preferably be a biologically compatible liquid such as, e.g., 0.9% normal saline, Ringer's solution, tissue culture media, serum, and plasma. The kit may also include means for delivering the carrier liquid to the enclosed defined volume in vivo, such as, e.g., a catheter, a lumen in a catheter, syringe, needle, etc.

The publications discussed herein are provided solely for their disclosure prior to the filing date of the present application. All publications mentioned herein are incorporated by reference to disclose and describe the methods and/or materials in connection with which the publications are cited. Nothing herein is to be construed as an admission that the present invention is not entitled to antedate such publication by virtue of prior invention.

Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. An implantable medical apparatus comprising:
an implantable medical device; and
a flexible magnetic sleeve located over an outer surface of the medical device, wherein the flexible sleeve is constructed of non-magnetic binder containing magnetic particles dispersed within the non-magnetic binder, wherein the magnetic sleeve is a separate and discrete article apart from the medical device.

2. An apparatus according to claim 1, wherein the implantable medical device comprises a tubular structure.

3. An apparatus according to claim 1, wherein the implantable medical device comprises a stent or a tubular graft.

4. An apparatus according to claim 1, wherein the magnetic sleeve is attached to the medical device.

5. An apparatus according to claim 1, wherein the magnetic sleeve comprises a tubular structure.

6. An apparatus according to claim 1, wherein the magnetic sleeve comprises a sheet.

7. An apparatus according to claim 1, wherein the non-magnetic binder is biodegradable.

8. An apparatus according to claim 1, wherein the magnetic sleeve comprises a porous wall.

9. An apparatus according to claim 1, further comprising adhesive on an exterior surface of the magnetic sleeve.

10. An apparatus according to claim 1 wherein the magnetic sleeve comprises a multilayer wall, and wherein at least one layer comprises a drug-eluting layer.

11. An apparatus according to claim 1 wherein the non-magnetic binder comprises elastomeric materials such that the sleeve exhibits elasticity.

12. An implantable medical apparatus comprising:
an implantable medical device that comprises a tubular structure; and
a flexible magnetic sleeve located proximate the medical device, wherein the flexible sleeve is constructed of non-magnetic binder containing magnetic particles dispersed within the non-magnetic binder, wherein the flexible magnetic sleeve is located inside the tubular structure of the implantable medical device, and wherein the magnetic sleeve is a separate and discrete article apart from the medical device.

13. An apparatus according to claim 12, wherein the implantable medical device comprises a stent or a tubular graft.

14. An apparatus according to claim 12, wherein the magnetic sleeve is attached to the medical device.

15. An apparatus according to claim 12, wherein the magnetic sleeve comprises a tubular structure.

16. An apparatus according to claim 12, wherein the magnetic sleeve comprises a sheet.

17. An apparatus according to claim 12, wherein the non-magnetic binder is biodegradable.

18. An apparatus according to claim 12, wherein the magnetic sleeve comprises a porous wall.

19. An apparatus according to claim 12, further comprising adhesive on an exterior surface of the magnetic sleeve.

20. An apparatus according to claim 12, wherein the magnetic sleeve comprises a multilayer wall, and wherein at least one layer comprises a drug-eluting layer.

21. An apparatus according to claim 12, wherein the non-magnetic binder comprises elastomeric materials such that the sleeve exhibits elasticity.

22. An implantable medical apparatus comprising:
an implantable medical device; and
a flexible magnetic sleeve located over an outer surface of the medical device, wherein the flexible sleeve is constructed of non-magnetic binder containing magnetic particles dispersed within the non-magnetic binder, wherein the sleeve is not a coating on the medical device.

* * * * *